United States Patent
Heckroth et al.

(10) Patent No.: US 9,757,492 B2
(45) Date of Patent: Sep. 12, 2017

(54) HYDROXY AMINO POLYMER AND USE THEREOF IN POLYUREA/POLYURETHANE TISSUE ADHESIVES

(71) Applicant: Adhesys Medical GmbH, Aachen (DE)

(72) Inventors: Heike Heckroth, Odenthal (DE); Christoph Eggert, Köln (DE); Jörg Hofmann, Krefeld (DE); Klaus Lorenz, Dormagen (DE); Edward Browne, Cologne (DE); Hartmut Nefzger, Pulheim (DE)

(73) Assignee: Adhesys Medical GmbH, Aachen (DE)

( * ) Notice: Subject to any disclaimer, the term of this patent is extended or adjusted under 35 U.S.C. 154(b) by 0 days.

(21) Appl. No.: 15/402,702

(22) Filed: Jan. 10, 2017

(65) Prior Publication Data

US 2017/0119921 A1    May 4, 2017

Related U.S. Application Data

(62) Division of application No. 14/365,233, filed as application No. PCT/EP2012/075825 on Dec. 17, 2012, now Pat. No. 9,580,540.

(30) Foreign Application Priority Data

Dec. 20, 2011 (EP) .................................... 11194417

(51) Int. Cl.

| C08G 18/46 | (2006.01) |
|---|---|
| A61L 24/00 | (2006.01) |
| A61L 24/04 | (2006.01) |
| C08G 63/91 | (2006.01) |
| C08G 18/73 | (2006.01) |
| C08G 18/10 | (2006.01) |
| C08G 18/48 | (2006.01) |
| C08G 18/38 | (2006.01) |

(52) U.S. Cl.
CPC ......... *A61L 24/046* (2013.01); *A61L 24/0042* (2013.01); *C08G 18/10* (2013.01); *C08G 18/3821* (2013.01); *C08G 18/485* (2013.01); *C08G 18/73* (2013.01)

(58) Field of Classification Search
CPC ... A61L 24/046; C08G 18/10; C08G 18/3821; C08G 18/4252; C08G 2230/00; C08G 63/91; C08L 75/04; C09J 175/04
See application file for complete search history.

(56) References Cited

U.S. PATENT DOCUMENTS

| 3,404,109 A | 10/1968 | Milgrom |
|---|---|---|
| 3,829,505 A | 8/1974 | Herold |
| 3,941,849 A | 3/1976 | Herold |
| 4,355,188 A | 10/1982 | Herold et al. |
| 4,550,194 A | 10/1985 | Reichel et al. |
| 4,721,818 A | 1/1988 | Harper et al. |
| 4,874,837 A | 10/1989 | Bershas et al. |
| 4,877,906 A | 10/1989 | Harper |
| 4,987,271 A | 1/1991 | Watabe et al. |
| 5,099,075 A | 3/1992 | Katz et al. |
| 5,158,922 A | 10/1992 | Hinney et al. |
| 5,391,722 A | 2/1995 | Chandalia et al. |
| 5,470,813 A | 11/1995 | Le-Khac |
| 5,587,182 A | 12/1996 | Sulzbach et al. |
| 5,597,390 A | 1/1997 | Loper |
| 5,739,192 A | 4/1998 | Blizzard et al. |
| 6,177,144 B1 | 1/2001 | Kranig et al. |
| 6,218,471 B1 | 4/2001 | Chenard et al. |
| 6,780,813 B1 | 8/2004 | Hofmann et al. |
| 7,008,900 B1 | 3/2006 | Hofmann et al. |
| 2005/0027145 A1 | 2/2005 | Hofmann et al. |
| 2005/0171002 A1 | 8/2005 | Mohanty et al. |
| 2008/0249279 A1 | 10/2008 | Arzt et al. |
| 2009/0191145 A1* | 7/2009 | Heckroth .............. A61L 24/046 424/78.06 |
| 2009/0221071 A1 | 9/2009 | Heckroth et al. |
| 2011/0245351 A1 | 10/2011 | Heckroth et al. |
| 2012/0019699 A1 | 1/2012 | Masuda et al. |

(Continued)

FOREIGN PATENT DOCUMENTS

| CN | 1119139 A | 3/1996 |
|---|---|---|
| CN | 2246064 Y | 1/1997 |

(Continued)

OTHER PUBLICATIONS

International Search Report for PCT/EP2012/075825 mailed Mar. 19, 2013.

*Primary Examiner* — Anna Falkowitz
(74) *Attorney, Agent, or Firm* — Drinker Biddle & Reath LLP

(57) ABSTRACT

The present invention relates to a process for producing a hydroxy amino polymer comprising the steps:

a) Reaction of an H functional starter compound bearing at least one Zerewitinoff active H atom with an unsaturated, cyclical carboxylic acid anhydride and at least one alkylene oxide compound for obtaining a prepolymer bearing hydroxyl groups, b) Addition of a primary amine and/or of ammonia to the double bond(s) of the prepolymer bearing hydroxyl groups obtained according to step a) for obtaining the hydroxy amino polymer, wherein the ratio of added amino groups to hydroxyl groups in a hydroxy amino polymer is at least 0.6. Furthermore, the invention relates to a hydroxy amino polymer, which can be achieved according to this process as well as a polyurea/polyurethane system, which contains such a hydroxy amino polymer.

18 Claims, No Drawings

(56) References Cited

U.S. PATENT DOCUMENTS

| | | |
|---|---|---|
| 2012/0178847 A1 | 7/2012 | Heckroth et al. |
| 2013/0123532 A1 | 5/2013 | Gurtler et al. |
| 2014/0329972 A1 | 11/2014 | Lorenz et al. |

FOREIGN PATENT DOCUMENTS

| | | |
|---|---|---|
| CN | 1170024 A | 1/1998 |
| DE | 3132258 A1 | 6/1982 |
| DE | 19508308 A1 | 9/1996 |
| DE | 19616984 A1 | 10/1997 |
| EP | 385619 A2 | 9/1990 |
| EP | 406440 A1 | 1/1991 |
| EP | 0700949 A2 | 3/1996 |
| EP | 0743093 A1 | 11/1996 |
| EP | 0761708 A2 | 3/1997 |
| EP | 1525244 A1 | 4/2005 |
| EP | 2095832 A1 | 9/2009 |
| EP | 2275466 A1 | 1/2011 |
| EP | 10163170 | 11/2011 |
| JP | 2002502925 A | 1/2002 |
| JP | 04089860 B2 | 5/2008 |
| JP | 4145123 B2 | 9/2008 |
| JP | 2008259660 A | 10/2008 |
| JP | 200922753 | 2/2009 |
| JP | 2009040772 A | 2/2009 |
| JP | 2009227753 A | 10/2009 |
| JP | 2012531506 A | 12/2012 |
| JP | 2015506383 A | 3/2015 |
| WO | WO-9740086 A1 | 10/1997 |
| WO | WO-9816310 A1 | 4/1998 |
| WO | WO-0047649 A1 | 8/2000 |
| WO | WO-0139883 A1 | 6/2001 |
| WO | WO-0180994 A1 | 11/2001 |
| WO | WO-2009106245 A2 | 9/2009 |
| WO | WO-2010066356 A2 | 6/2010 |
| WO | WO-2010090345 A1 | 8/2010 |

* cited by examiner

HYDROXY AMINO POLYMER AND USE THEREOF IN POLYUREA/POLYURETHANE TISSUE ADHESIVES

CROSS-REFERENCE TO RELATED APPLICATIONS

This application is a divisional application of U.S. patent application Ser. No. 14/365,233, filed Jun. 13, 2014, which is a national stage application (under 35 U.S.C. §371) of PCT/EP2012/075825, filed Dec. 17, 2012, which claims benefit of European Application No. 11194417.9, filed Dec. 20, 2011, both of which are incorporated herein by reference in their entirety.

The present invention relates to a process for producing a hydroxy amino polymer, which can be achieved according to this process, as well as a polyurea/polyurethane system containing such a hydroxy amino polymer.

Tissue adhesives are commercially available in various forms. This includes the cyanoacrylates, Dermabond® (octyl-2-cyanoacrylate) and Histoacryl Blue® (butyl cyanoacrylate). Cyanoacrylates, however, require dry subsurfaces for efficient adhesion. These types of adhesives fail in the case of severe bleeding.

Biological adhesives, such as BioGlue®, a mixture of glutaraldehyde and bovine serum albumin, various collagens and gelatin-based systems (FloSeal®) as well as fibrin adhesive (Tissucol), are available as an alternative to cyanoacrylates. The primary role of these systems is to stop bleeding (hemostasis). In addition to high costs, fibrin adhesives feature a relatively weak adhesive strength and rapid breakdown, such that they can only be used for less severe injuries on tissue that is not stretched. Collagen and gelatin-based systems, such as FloSeal® work exclusively to attain hemostasis. Additionally, there is always a risk of infection with biological systems as fibrin and thrombin are extracted from human material and collagen and gelatin from animal material. Furthermore, biological materials must be stored in refrigeration, therefore they cannot be used for emergency care, such as in disaster areas, for military exercises, etc. In this case, trauma injuries can be treated with QuikClot® or QuikClot ACS+™, which are a mineral granulate that is applied to the wound in an emergency and causes coagulation by withdrawing water. QuikClot® produces a highly exothermic reaction, which leads to burns. QuikClot ACS+™ is gauze, into which salt is embedded. The system must be firmly pressed against the wound to stop bleeding. WO 2009/106245 A2 highlights the production and use of polyurea/polyurethane systems as tissue adhesive. The systems revealed therein comprise at least two components. This involves an amino functional aspartic acid ester and an isocyanate functional prepolymer, which can be attained through the reaction of aliphatic polyisocyanates with polyester polyols. The two-component polyurea/polyurethane systems described can be used as tissue adhesive for closing wounds in human and animal cell structures. In doing so, a very positive adhesive result can be achieved.

To ensure that both components of the polyurea/polyurethane system can mix well, the viscosity of the components at 23° C. should—to the extent possible—be less than 10,000 mPa. Prepolymers with NCO functionalities have a respectively low viscosity of less than 3. If said prepolymers are used, it is necessary to use an aspartic acid ester with an amino functionality of more than two as a second component because otherwise a polymeric network cannot be produced. However, this is necessary so that said polyurea/polyurethane system or an adhesive joint consisting thereof has the desired mechanical properties, such as elasticity and strength. Moreover, there is a disadvantage to using difunctional aspartic acid ester, namely that the hardening time takes up to 24 hours, wherein the polyurea/polyurethane system itself remains tacky in many cases after this period, i.e. it is not "tack-free". Furthermore, the resulting adhesives are primarily designed for topical applications and are not biologically degradable in the body within a short period, e.g. within 6 months or less. However, for applications within the body, an adhesive system should meet this requirement.

WO 2010/066356 highlights adhesive systems for medical applications, in which isocyanate-terminated prepolymers are reacted or hardened with secondary diamines. The disadvantages already mentioned in relation to WO 2009/106245 A2 occur in this case as well.

Furthermore, we are familiar with polymers, which are amine functional and carry hydroxyl groups (so-called hydroxy amino polymers). Such compounds are gaining increasing interest in certain areas of application, especially in the polyurethane industry. The reason for this lies in the fact that new property and treatment profiles can be produced through the presence of two different types of functional groups, namely amine functionalities as well as hydroxyl groups. Thus, there is the possibility of influencing the timing of the hardening process in a desired manner, for example, through the combination of amino groups, which are significantly more reactive compared to isocyanate groups, with less reactive hydroxyl groups, which was previously not possible or only to a limited extent with the presence of only one type of the aforementioned isocyanate-reactive functional groups.

In general, the amino functionality of hydroxy amino polymers can be introduced in macromolecules by adding primary amines or ammonia to low-electron double bonds, for instance, of a (meth)acrylate type. We are familiar with the addition of amines to polymers containing (meth)acrylate groups, to polyether containing (meth)acrylate groups in themselves, for example, such processes are mentioned in U.S. Pat. No. 5,739,192 A1, U.S. Pat. No. 5,597,390 A1, US 2005/0171002 A1, DE 196 16 984 A1, DE 195 08 308 A1, WO 2010/090345 A1, JP 2009/22753 A1, and JP 04089860 A1.

In contrast, obtaining state of the art precursor compounds containing low-electron double bonds is either not described or occurs via condensation reactions taking place according to statistic logic, for example, via the esterification of acrylic acid with difunctional polyethers or the reaction of acryloyl chloride with difunctional polyethers.

These described processes share the common feature that the introduction of double bonds into the precursor compounds of hydroxy amino polymers occurs at the expense of the number of hydroxy functions. Thus, these processes do not allow the original hydroxy functionality, which existed in polyether molecules in general through the functionality of starter molecules used for the production of polyether, to be obtained during the introduction of amino functionality. Additionally, the aforementioned printed materials do not reveal that these compounds can be used for adhesion in medical applications.

In this context, the goal of the invention was to provide an isocyanate-reactive component for a polyurea/polyurethane system, which can be positively mixed with a prepolymer having an NCO functionality of less than 3 and can be quickly reacted with said prepolymer through the formation of a three-dimensional polyurea/polyurethane network. Furthermore, said isocyanate-reactive component should enable the provisioning of a polyurea/polyurethane system for tissue adhesives, which biologically degrade in the body within a short period after the wound has completely healed, e.g. within 6 months or less. In doing so, the hardened system pursuant to ISO 10993 should not have cytotoxicity when used in humans.

This task is solved through a process for the production of a hydroxy amino polymer comprising the steps:
a) Reaction of an H functional starter compound bearing at least one Zerewitinoff active H atom with an unsaturated, cyclical carboxylic acid anhydride and at least one alkylene oxide compound for obtaining a prepolymer bearing hydroxyl groups,
b) Addition of a primary amine and/or of ammonia to the double bond(s) of the prepolymer bearing hydroxyl groups obtained according to step a) for obtaining the hydroxy amino polymer,
wherein the ratio of added amino groups to hydroxyl groups in a hydroxy amino polymer is at least 0.6.

The invention also relates to a hydroxy amino polymer, which can be produced according to the process pursuant to the invention. As a result of the polymer analogous reaction(s) based on the process pursuant to the invention, in practice, the hydroxy amino polymer normally depicts a mixture of various structures, which—from a statistical perspective—has the ratio pursuant to the invention of amino groups to hydroxyl groups.

In the process, the indefinite article "a", "an", etc. means that respectively even several of these components can be optionally reacted with each other in the process pursuant to the invention.

The hydroxy amino polymer pursuant to the invention has an amino functionality of >1, preferably less than 2, at least 3 or more, and thus capable of quickly forming a three-dimensional polyurea/polyurethane network with prepolymers of an NCO functionality of 2 or more, and preferably of 3.

In the process, the aforementioned compound has the added benefit that it—from a statistical perspective as well—bears more than one terminal hydroxy group in addition to amino functionalities. These groups are likewise NCO reactive and additionally facilitate the rapid development of the polymer network. This network is distinguished by high elasticity, strength, adhesive strength, and a lack of cytotoxicity. Moreover, the network is no longer sticky, i.e. "tack-free" after only a short period.

In addition, the compound pursuant to the invention can be easily mixed with a prepolymer because it has a viscosity of less than 10,000 mPa at 23° C. In this way, the compound can also be used in 2-component spray systems, in which the individual components are only mixed together in a mixing nozzle upon being sprayed.

A provision is made within the scope of the aforementioned process that the hydrogen functional starter compound bears at least one Zerewitinoff active H atom. The Zerewitinoff active H atom indicates an acidic H atom or "active" H atom within the scope of the present invention. It can be identified in a conventional manner through reactivity with a respective Grignard reagent. The quantity of Zerewitinoff active H atoms is typically measured through the release of methane, which occurs according to a following reaction equation (formula 1) in a reaction of the substance to be tested with methylmagnesium bromide ($CH_3$—MgBr):

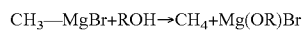

(1)

Zerewitinoff active H atoms typically originate from C—H acidic, organic groups, —OH, —SH, —$NH_2$ or —NHR with R as an organic radical, and —COOH.

In addition to hydroxy functional starters, which are to be preferably used, amino functional starters may also be used.

Examples for hydroxy functional starter compounds are methanol, ethanol, 1-Propanol, 2-Propanol and higher aliphatic monols, particularly fatty alcohols, phenol, alkyl-substituted phenols, propylene glycol, ethylene glycol, diethylene glycol, dipropylene glycol, 1,2-Butanediol, 1,3-Butanediol, 1,4-Butanediol, hexanediol, pentanediol, 3-Methyl-1,5-pentanediol, 1,12-Dodecanediol, glycerin, trimethylolpropane, pentaerythritol, sorbitol, sucrose, hydroquinone, brenzcatechol, resorcinol, bisphenol F, bisphenol A, 1,3,5-Trihydroxybenzene, as well as condensates containing methylol groups consisting of formaldehyde and phenol or urea. Highly functional starter compounds may also be used based on hydrogenated starch hydrolysis products. These are described, for example, in EP 1525244 A1.

Examples for H functional starter compounds containing amino groups are ammonia, ethanolamine, diethanolamine, triethanolamine, isopropanolamine, diisopropanolamine, ethylenediamine, hexamethylenediamine, aniline, the isomers of toluidine the isomers of diaminotoluene, the isomers of diaminodiphenylmethane as well as more solid products being made with the condensation of aniline with formaldehyde to diaminodiphenylmethane, in addition to condensates comprised of formaldehyde and melamine containing methylol groups, as well as Mannich bases.

Additionally, ring-opening products from cyclical carboxylic acid can also be used as starter compounds in hydrides and polyols. Examples are ring-opening products comprised of phthalic acid anhydride or succinic acid anhydride on the one hand, and ethylene glycol, diethylene glycol, 1,2-butanediol, 1,3-butanediol, 1,4-butanediol, hexanediol, pentanediol, 3-methyl-1,5-pentanediol, 1,12-dodecanediol, glycerin, trimethylolpropane, pentaerythritol or sorbitol on the other. In addition, it is also possible to used single or multifunctional carboxylic acid directly as starter compounds.

Furthermore, prefabricated alkylene oxide addition productions of said starter compounds, i.e. polyether polyols preferably with OH values of 5 to 1000 mg KOH/g, preferably 10 to 1000 mg KOH/g, can also be used in the process as starter compounds or added to the reaction mixture. It is also possible to use polyester polyols as co-starters preferably with OH values in the range of 6 to 800 mg KOH/g in the process pursuant to the invention. In this regard, suitable polyester polyols can be produced according to conventional methods, for example, from organic dicarboxylic acids with 2 to 12 carbon atoms and multivalent alcohols, preferably diols with 2 to 12 carbon atoms, preferably 2 to 6 carbon atoms.

Moreover, as H functional starter substances, polycarbonate polyols, polyester carbonate polyols or polyether carbonate polyols, preferably polycarbonate diols, polyester carbonate diols or polyether carbonate diols, preferably respectively having OH values in the range of 6 to 800 mg KOH/g, can be used as starters or co-starters. These are produced, for example, through a reaction of phosgene, dimethyl carbonate, diethyl carbonate or diphenyl carbonate with di or higher functional alcohols or polyester polyols or polyether polyols.

In step a) of the process pursuant to the invention, preferably H functional starter compounds having hydroxy groups and being free of amino groups serve as bearers of active hydrocarbons, such as methanol, ethanol, 1-propanol, 2-propanol and higher aliphatic monols, particularly fatty alcohols, phenol, alkyl-substituted phenols, propylene glycol, ethylene glycol, diethylene glycol, dipropylene glycol, 1,2-butanediol, 1,3-butanediol, 1,4-butanediol, hexanediol, pentanediol, 3-methyl-1,5-pentanediol, 1,12-Dodecanediol, glycerin, trimethylolpropane, pentaerythritol, sorbitol, sucrose, hydroquinone, brenzcatechol, resorcinol, bisphenol F, bisphenol A, 1,3,5-trihydroxybenzene, condensates consisting of formaldehyde and phenol containing methylol groups and hydrogenated starch hydrolysis products. Mixtures of H functional starter compounds can be used as well. If an H functional starter compound is referred to in the following, mixtures of H functional starter compounds are principally meant as well, insofar as this is not expressly precluded.

All compounds known to experts as such are worth consideration for the unsaturated, cyclical carboxylic acid anhydride used within the scope of the process pursuant to the invention. These are, for example, unsaturated, cyclical dicarboxylic acid anhydrides, such as maleic anhydride, tetrahydrophthalic anhydride, particularly 3,4,5,6-tetrahydrophthalic anhydride as well as combinations thereof.

If multiple unsaturated, cyclical carboxylic acid anhydrides are used, they may likewise be dispensed individually, in the mixture or in blocks. It is also possible to added said cyclical carboxylic acid anhydride or the cyclical carboxylic acid anhydrides to the reaction mixture together with the alkylene oxide(s) or as a separate block without simultaneously dispensing alkylene oxide. If an unsaturated, cyclical carboxylic acid anhydride is referred to in the following, mixtures of unsaturated, cyclical carboxylic acid anhydrides are principally meant as well, insofar as this is not expressly specified.

As an alkylene oxide compound usable pursuant to the invention, such substitutes can be selected, which have 2 to 24 carbon atoms, particularly 2 to 12 carbon atoms, more preferably 2 to 6 carbon atoms, as well as the combination of various alkylene oxide compounds of the aforementioned type. Alkylene oxides with 2 to 24 carbon atoms are those, for example, involving one or more compounds selected from a group comprised of ethylene oxide, propylene oxide, 1-butene oxide, 2,3-butene oxide, 2-methyl-1,2-propenoxide (isobutene oxide), 1-pentene oxide, 2,3-pentene oxide, 2-methyl-1,2-butene oxide, 3-methyl-1,2-butenoxid, 1-hexene oxide, 2,3-hexene oxide, 3,4-hexene oxide, 2-methyl-1,2-pentene oxide, 4-methyl-1,2-pentene oxide, 2-ethyl-1,2-butene oxide, 1-heptene oxide, 1-octene oxide, 1-nonene oxide, 1-decene oxide, 1-undecene oxide, 1-dodecene oxide, 4-methyl-1,2-pentene oxide, butadiene monoxide, isoprene monoxide, cyclopentene oxide, cyclohexene oxide, cycloheptene oxide, cyclooctene oxide, styrene oxide, methylstyrene oxide, pinene oxide, one or more-fold epoxy-enhanced fats as mono, di, and triglycerides, epoxy-enhanced fatty acids, $C_1$-$C_{24}$-esters from epoxy-enhanced fatty acids, epichlorohydrin, glycidol, and derivatives of glycidol, such as methyl glycidyl ether, ethyl glycidyl ether, 2-ethylhexyl glycidyl ether, allyl glycidyl ether, glycidyl methacrylate as well as epoxy functional alkyloxysilanes, such as 3-glycidoxypropyltrimethoxysilane, 3-glycidoxypropyltrimethoxysilane, 3-glycidoxypropyltripropoxysilane, 3-glycidoxypropyl methyldi methoxysi lane, 3-glycidoxypropyl methyldiethoxysilane, and 3-glycidoxypropyltriisopropoxysilane.

Ethylene oxide and/or propylene oxide are preferably used as alkylene oxide. Ethylene oxide in shares of 40% by weight or more is particularly preferably used, preferably in shares of 40 to 90% by weight in relation to the overall mass of the alkylene oxide to be dispensed. The alkylene oxides can be dispensed individually, in a mixture or in blocks. If an alkylene oxide or an alkylene oxide compound is referred to in the following, mixtures of alkylene oxide or alkylene oxide compounds or the dispensing of various alkylene oxides or alkylene oxide compounds in blocks are principally meant as well, insofar as this is not expressly specified.

In the case of the process pursuant to the invention, an additional provision is made that the molar ratio between carboxylic acid anhydride and the number of Zerewitinoff active H atoms of the starter compound is selected so that, to the extent possible, all Zerewitinoff active H atoms are reacted. The molar ration between carboxylic acid anhydride and the number of Zerewitinoff active H atoms of the H functional starter compound can be approx. 1:1 to 1.5:1, particularly 1:1 to 1.2:1.

Incidentally, the processes pursuant to the invention are not limited to the use of the aforementioned monomers. Thus, it is possible, for example, that at least one comonomer is reacted, which is in particular selected from lactones, lactides, saturated or aromatic, cyclical carboxylic acid anhydrides, cyclical carbonates and/or carbon dioxide. In this manner, the property profile of the hydroxy amino polymer obtained can be further modified, for example, in relation to its reactivity with respect to isocyanate groups, it polarity as well as other chemical or physical properties of hydroxy amino polymers or its reaction product with a polyisocynate. This comonomer is preferably added in step a) of the process pursuant to the invention.

Among other things, a provision is made within the scope of the process pursuant to the invention that a primary amine of ammonia is added to the double bond of the prepolymer bearing hydroxyl groups. Suitable amines are, for example, ammonia, aliphatic, cycloaliphatic, and/or araliphatic monoamines with one primary amino group, such as methylamine, ethylamine, diethylamine, 1-aminopropane, 2-aminopropane, 1-aminobutane, 2-aminobutane, isobutylamine, 1-aminohexane, 2-ethyl-1-aminohexane, dodecylamine, octadecylamine, cyclohexylamine, and benzylamine; aliphatic, cycloaliphatic, and/or araliphatic diamines with one primary amino group and one secondary amino group, wherein said secondary amino group can also be a part of a ring system, such as N-methylethylenediamine, N-methylpropylenediamine, N-(2-aminoethyl) piperazine, and 3-amino-1,2,4-triazol; aliphatic, cycloaliphatic, and/or heterocyclic diamines with one primary and one tertiary amino group, and potentially one secondary amino group, such as N,N-dimethylethylenediamine, N,N-dimethyl-1,3-diaminopropane, N,N-dimethyl-1,8-diaminooctane, N,N-dimethyl-1,4-diaminocyclohexane, and aliphatic amines with two primary and at least one secondary amino group, such as diethylenetriamine, triethylenetetramine, tetraethylenepentamine, and bis-(3-aminopropyl)-amine. Furthermore, amines containing hydroxy groups in addition to primary amino groups, such as ethanolamine or isopropanolamine, are suitable for the process pursuant to the invention.

(Cyclo)aliphatic diamines are likewise suitable. These involve compounds with two primary amino groups with a general formula $NH_2$—R—$NH_2$, in which R represents an aliphatic or cycloaliphatic radical with 2 to 21, preferably 2 to 15, and particularly preferably 2 to 10 carbon atoms. Examples for this are ethylenediamine, 1,2- and 1,3-propylendiamine, 1,4-diaminobutane, 1,6-diaminohexane, 2,2,4- and 2,4,4-trimethyl-1,6-diaminohexane, 1,4-diaminocyclohexane, 1,5-diamino-2-methylpentane, 5-amino-1-aminomethyl-1,3,3-trimethylcyclohexane (isophorone diamine), bis-(4-aminocyclohexyl)-methane, bis-(4-amino-3-methylcyclohexyl)-methane, 1-amino-1-methyl-3(4)-aminomethyl cyclohexane, bis-(4-Amino-3,5-diethylcyclohexyl)-methane, bis-aminomethyl-hexahydro-4,7-methano-indane, 2,3-, 2,4- and 2,6-diamino-1-methylcyclohexane or mixtures of these diamines. Naturally, the specified mono and oligoamines may also be used as a mixture as well. If an amine to be added is referred to in the following, mixtures of amines to be added are principally meant as well, insofar as not expressly specified.

The molar ratio of primary amino groups to double bonds capable of addition is preferably 0.01:1 to 1.1:1, preferable 0.1:1 to 1.1:1, particularly preferably 0.5:1 to 1.1:1, and very particularly preferably 1:1 to 1.1:1. The reaction can be conducted catalyzed or uncatalyzed. Suitable catalysts are, for example, copper acetate, tin chloride or acetic acid. The amines are preferably added without catalytic additives. A reaction temperature range suitable for this step is, for example, that from 0° C. to 150° C., preferably from 10° C. to 100° C., and particularly preferably 20° C. to 80° C.

According to a preferred embodiment of the process pursuant to the invention, the molar ratio between the alkylene oxide compound and carboxylic acid anhydride is set to at least 1:1, preferably to at least 2:1, particularly preferably to at least 2.5:1. With this embodiment of the process pursuant to the invention, it is possible to synthesize hydroxy amino polymers with a medium distance of more than seven covalent bond lengths between the amine functionality and the hydroxyl group.

In another configuration of the process pursuant to the invention, the ratio of added amino groups to hydroxyl groups in the hydroxy amino polymer is 0.8 to 2.5, particularly 0.9 to 2.0, and preferably 0.95 to 1.8. As a result, the interconnectivity of the hydroxy amino polymer can still be additionally increased in a reaction with a polyfunctional NCO prepolymer.

With regard to the OH functionality of the hydroxy amino polymer, it can be 1.5 to 6 in a preferred way, particularly 1.7 to 4, and particularly preferably 1.8 to 3.

A provision is made within the scope of the process pursuant to the invention that an H functional starter compound bearing at least one Zerewitinoff active H atom is used. This compound may have 1 to 35 Zerewitinoff active H atoms in a preferred way, particularly 1 to 8.

The mol mass of the H functional starter compound may vary throughout broad ranges. Thus, the H functional starter compound may have, for example, a number average molar mass of 17 to 10,000 g/mol. In other words, therefore, the scope of the present invention provides that it is necessary to start from a monomer or short-chained starter compound, e.g. ammonia, or even from a polymeric starter compound.

Step a) First Process Alternative:

According to a first alternative, it is initially possible to convert the H functional starter compound with an initial quantity of alkylene oxide compound and then with an unsaturated, cyclical carboxylic acid anhydride and an additional quantity of said alkylene oxide compound. Thus, in this case, the chain length of the H functional starter compound is initially enlarged before the reaction occurs with said unsaturated, cyclical carboxylic acid anhydride and an additional quantity of alkylene oxide compound. The H functional starter compound largely retains the number of its Zerewitinoff active H atoms upon increasing the length of the chain as initially only oxyalkylene units are added to the original H functional starter compound, wherein an H functional starter compound is achieved with a higher molecular weight.

This method is particularly suitable if we start from an H functional starter compound with a number average molar mass of 17 to 1200 g/mol, particularly from 62 to 1000 g/mol. This H functional starter compound can then be formed by adding the alkylene oxide compound, for example, to a number average molar mass of 200 to 20000 g/mol, preferably from 600 to 10000 g/mol. This method is beneficial because structures can be produced as a result, for which the distance between the amino functionality and hydroxyl group may be more than 6 or 7 covalent bond lengths.

In a further configuration of the process pursuant to the invention, the reaction of the H functional starter compound is performed with the unsaturated, cyclical carboxylic acid anhydride and/or the addition of the alkylene oxide compound by using a double metal cyanide catalyst (DMC catalyst), wherein said DMC catalyst preferably contains zinc hexacyanocobaltate (III), zinc hexacyanoiridate (III), zinc hexacyanoferrate (III), and cobalt (II) hexacyanocobaltate (III).

The process may be configured, for instance, such that after the abreaction of a dispensed alkylene oxide compound, unsaturated, cyclical carboxylic acid anhydride is added, for example, approx. 1 mol of carboxylic acid anhydride per mol of OH groups present. Subsequently, any desired quantity of alkylene oxide compounds is added again to obtain the prepolymer bearing the hydroxyl groups. The aforementioned reaction sequence can be repeated once or more times, such that any desired number, particularly more than one double bond per Zerewitinoff active H atom, can be integrated into the prepolymer. Thus, for example, 2 or more, particularly 3 or more amino functionalities per Zerewitinoff active H atom can be introduced to the double bonds through addition. Naturally, the double bonds can also be introduced into the prepolymer through parallel dispensing of one or more alkylene oxide compounds and one or more unsaturated, cyclical carboxylic acid anhydrides to one or multiple starter compounds bearing Zerewitinoff active H atoms. This parallel dispensing of one or more alkylene oxide compounds and one or more unsaturated, cyclical carboxylic acid anhydrides may occur from the onset or after one pure alkylene oxide block was dispensed for said starter compound bearing Zerewitinoff active H atoms.

The double bonds to the polymer chains of the prepolymer are distributed when the alkylene oxide compound(s) and unsaturated, cyclical carboxylic acid anhydride are dispensed pursuant to statistical logic, particularly the blocks of polyether chains based on alkylene oxide elements are subject to a broader length distribution.

The process pursuant to the invention provides that a double metal cyanide catalyst (DMC catalyst) is used in step a), i.e. with the reaction of the H functional starter compound with the unsaturated, cyclical carboxylic acid anhydride and/or the addition of the alkylene oxide compound. In doing so, mixtures of various DMC catalysts may be used as well.

Suitable DMC catalysts are generally known from the state of the art and are, for example, published in U.S. Pat. No. 3,404,109 A1, U.S. Pat. No. 3,829,505 A1, U.S. Pat. No. 3,941,849 A1, and U.S. Pat. No. 5,158,922 A1.

DMC catalysts, which are described, for example, in U.S. Pat. No. 5,470,813 A1, EP 700949 A1, EP 743 093 A1, EP 761 708 A1, WO 97/40086 A1, WO 98/16310 A1, and WO 00/47649 A1 have a very high level of activity in the polymerization of alkylene oxides and, potentially, the copolymerization of alkylene oxides and unsaturated, cyclical carboxylic acid anhydrides and enable the production of polyether polyols with very minimal catalyst concentrations (25 ppm or less), such that a separation of the catalyst from the finished product is generally no longer necessary. A typical example is the highly active DMC catalysts described in EP 700 949 A1, which contain an additional polyether with a number average molecular weight greater than 500 g/mol in addition to a double metal cyanide compound, such as zinc hexacyanocobaltate (III) and an organic complex ligand, such as tert-Butanol. It is also possible to use the alkaline DMC catalysts published in EP application number 10163170.3.

Cyanide-free metallic salts suitable for the production of double metal cyanide compounds preferably have a general formula (III), $$M(X)_n \tag{III}$$

wherein

M is selected from the metal cations $Zn^{2+}$, $Fe^{2+}$, $Ni^{2+}$, $Mn^{2+}$, $Co^{2+}$, $Sr^{2+}$, $Sn^{2+}$, $Pb^{2+}$, and $Cu^{2+}$, M $Zn^{2+}$, $Fe^{2+}$, $Co^{2+}$ or $Ni^{2+}$ is preferred, X represents one or more (i.e. various) anions, which is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;

n is 1 if X=sulfate, carbonate or oxalate, and n is 2 if X=halogenide, hydroxide, cyanate, thiocyanate, isocyanate, isothiocyanate or nitrate.

Additionally suitable cyanide-free metallic salts have a general formula (IV), $$M_r(X)_3 \tag{IV}$$

wherein

M is selected from the metal cations $Fe^{3+}$, $Al^{3+}$, and $Cr^{3+}$,

X represents one or various types of anions, wherein the anion is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;

r is 2 if X=sulfate, carbonate or oxalate, and r is 1 if X=halogenide, hydroxide, cyanate, thiocyanate, isocyanate, isothiocyanate, carboxylate or nitrate.

Other suitable cyanide-free metallic salts have a general formula (V), $$M(X)_s \tag{V}$$

wherein

M is selected from the metal cations $Mo^{4+}$, $V^{4+}$, and $W^{4+}$

X represents one or various types of anions, wherein the anion is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;

s is 2 if X=sulfate, carbonate or oxalate, and s is 4 if X=halogenide, hydroxide, cyanate, thiocyanate, isocyanate, isothiocyanate, carboxylate, or nitrate.

Likewise suitable cyanide-free metallic salts have a general formula (VI), $$M(X)_t \tag{VI}$$

wherein

M is selected from the metal cations $Mo^{6+}$ and $W^{6+}$

X represents one or various types of anions, wherein the anion is preferably selected from the group of halogenides (i.e. fluoride, chloride, bromide, iodide), hydroxide, sulfate, carbonate, cyanate, thiocyanate, isocyanate, isothiocyanate, carboxylate, oxalate, and nitrate;

t is 3 if X=sulfate, carbonate or oxalate, and t is 6 if X=halogenide, hydroxide, cyanate, thiocyanate, isocyanate, isothiocyanate, carboxylate or nitrate, Examples of suitable cyanide-free metallic salts are zinc chloride, zinc bromide, zinc iodide, zinc acetate, zinc acetylacetonate, iron(II)sulfate, iron(II)bromide, iron(II)chloride, cobalt(II)chloride, cobalt(II)thiocyanate, nickel(II)chloride, and nickel(II)nitrate. Mixtures of various metallic salts may be used as well.

Metal cyanide salts suitable for the production of double metal cyanide compounds preferably have a general formula (VII)

$$(Y)_a M'(CN)_b (A) \tag{VII}$$

wherein

M' is selected from one or more metal cations of the group comprised of Fe(II), Fe(III), Co(II), Co(III), Cr(II), Cr(III), Mn(II), Mn(III), Ir(III), Ni(II), Rh(III), Ru(II), V(IV), and V(V), M' is preferably one or more metal cations of the group comprised of Co(II), Co(III), Fe(II), Fe(III), Cr(III), Ir(III), and Ni(II), Y is selected from one or more metal cations of the group comprised of alkaline metal (i.e. $Li^+$, $Na^+$, $K^+$, $Rb^+$, $Cs^+$, and alkaline earth metal (i.e. $Be^{2+}$, $Ca^{2+}$, $Mg^{2+}$, $Sr^{2+}$, $Ba^{2+}$), A is selected from one or more anions of the group comprised of halogenides (i.e. fluoride, chloride, bromide, iodide), hydroxide, sulfate, carbonate, cyanate, thiocyanate, isocyanate, isothiocyanate, carboxylate, oxalate or nitrate, and a, b, and c are whole numbers, wherein the values for a, b, and co are selected in such a way that there is electroneutrality of the metal cyanide salt; a is preferably 1, 2, 3 or 4; b is preferably 4, 5 or 6; c preferably has the value of 0.

Examples of suitable metal cyanide salts are potassium hexacyanocobaltate(III), potassium hexacyanoferrate(II), potassium hexacyanoferrate(III), calcium hexacyanocobaltate(III), and lithium hexacyanocobaltate(III).

Preferred double metal cyanide compounds, which are contained in DMC catalysts pursuant to the invention, are compounds of a general formula (VIII)

$$Mx[M'x,(CN)y]z \tag{VIII},$$

in which M is defined as in formula (III) to (VI) and

M' is defined as in formula (VII), and x, x', y, and z are whole numbers and selected in such a manner that there is electroneutrality of the double metal cyanide compound.

Preferably x=3, x'=1, y=6, and z=2,

M=Zn(II), Fe(II), Co(II) or Ni(II) and

M'=Co(III), Fe(III), Cr(III) or Ir(III).

Examples of preferably used double metal cyanide compounds are zinc hexacyanocobaltate (III), zinc hexacyanoiridate (III), zinc hexacyanoferrate (III), and cobalt (II) hexacyanocobaltate (III). Additional examples of suitable double metal cyanide compounds can be found, e.g. U.S. Pat. No. 5,158,922 A1. Zinc hexacyanocobaltate (III) is particularly preferably used.

The organic complex ligands added to during the production of DMC catalysts are published, for example, in U.S. Pat. No. 5,158,922 A1, U.S. Pat. No. 3,404,109 A1, U.S. Pat. No. 3,829,505 A1, U.S. Pat. No. 3,941,849 A1, EP 700949 A1, EP 761708 A1, JP 4145123 A1, U.S. Pat. No. 5,470,813 A1, EP 743 093 A1, and WO 97/40086 A1. Water-soluble organic compounds with heteroatoms, such as oxygen, nitrogen, phosphorus or sulfur, which can form complexes with the double metal cyanide compound, are, for instance, used as organic complex ligands. Preferred organic complex ligands are alcohols, aldehydes, ketones, ethers, esters, amides, urea, nitriles, sulfides, and their mixtures. Particularly preferred organic complex ligands are aliphatic ethers (such as dimethoxyethane), water soluble aliphatic alcohols (such as ethanol, isopropanol, n-butanol, iso-butanol, sec-butanol, tert-butanol, 2-methyl-3-buten-2-ol, and 2-methyl-3-butyn-2-ol), compounds, which contain aliphatic or cycloaliphatic ether groups as well as aliphatic hydroxyl groups (such as ethylene glycol-mono-tert-butyl ether, diethylene glycol-mono-tert-butyl ether, tripropylene glycol-mono-methyl ether, and 3-methyl-3-oxetane-methanol). Highly preferred organic complex ligands are selected from one or more compounds of the group comprised of dimethoxyethane, tert-Butanol, 2-methyl-3-buten-2-ol, 2-methyl-3-butyn-2-ol, ethylene glycol-mono-tert-butyl ether, and 3-methyl-3-oxetane-methanol.

One or more complex-forming component(s) from the compound classes of polyethers, polyesters, polycarbonates, polyalkylene glycol sorbitan esters, polyalkylene glycol glycidyl ethers, polyacrylamide, poly(acrylamide-co-acrylic acid), polyacrylic acid, poly(acrylic acid-co-maleic acid), polyacrylonitrile, poly alkyl acrylates, poly alkyl methacrylates, polyvinyl methyl ethers, polyvinyl ethyl ethers, polyvinyl acetate, polyvinyl alcohol, poly-N-vinylpyrrolidone, poly(N-vinylpyrrolidone-co-acrylic acid), poly vinyl methyl ketone, poly(4-vinylphenol), poly(acrylic acid costyrene), oxazoline polymers, polyalkylene imines, maleic acid and maleic acid anhydride copolymers, hydroxyethyl cellulose and polyacetylene or of glycidyl ethers, glycosides, carboxylic acid esters of polyvalent alcohols, bile acids or their salts, esters or amides, cyclodextrins, phosphorus compounds, $\alpha,\beta$-unsaturated carboxylic acid esters or ionic surface or interfacial-active compounds are optionally used for the production of DMC catalysts preferred pursuant to the invention.

Preferably, the aqueous solutions of metallic salt (e.g. zinc chloride) used for producing the DMC catalysts preferred pursuant to the invention in the first step in stoichiometric surplus (at least 50 mol %) in relation to metal cyanide salt, (i.e. at least one molar ratio of cyanide-free metallic salt to metal cyanide salt of 2.25 to 1.00) and the metal cyanide salt (e.g. potassium hexacyanocobaltate) in the presence of the organic complex ligands (e.g. tert-butanol) are reacted, such that a suspension forms containing the double metal cyanide compound (e.g. zinc hexacyanocobaltate), water, surplus cyanide-free metallic salt, and the organic complex ligands. In the process, the organic complex ligand may present in the aqueous solution of the cyanide-free metallic salt and/or the metal cyanide salt or it is directly added to the suspension obtained after precipitation of the double metal cyanide compound. It has been proven to be beneficial to mix the aqueous solution of the cyanide-free metallic salt and the metal cyanide salt and the organic complex ligand while stirring vigorously. The suspension formed in the first step is then optionally treated with an additional complex forming component. In this process, the complex-forming component is preferably used in a mixture with water and organic complex ligands. A preferred method for conducting the first step (i.e. production of the suspension) occurs through the use of a mixing nozzle, particularly preferably through the use of a spray dispersant, as described in WO 01/39883 A1.

In the second step, the solid matter is isolated (i.e. the preliminary stage of the catalyst pursuant to the invention) from the suspension through convention techniques, such as centrifugation or filtration.

In a preferred embodiment type for producing the catalyst, the isolated solid matter is subsequently washed in a third step of the process with an aqueous solution of the organic complex ligand (e.g. by means of re-suspension and subsequent re-isolation through filtration and centrifugation). In this manner, for example, water-soluble byproducts, such as potassium chloride, can be removed from the catalyst pursuant to the invention. The quantity of organic complex ligand in the aqueous washing solution is preferably between 40 and 80% by weight in relation to the overall solution.

In the third step of the aqueous washing solution, an additional complex-forming component, preferably in the range between 0.5 and 5% by weight in relation to the overall solution, is optionally added.

Furthermore, it is beneficial to wash the isolated solid matter more than once. In this regard, e.g. the first washing process can be repeated. However, it is preferable to not use aqueous solutions for additional washing processes, e.g. a mixture of organic complex ligands and another complex forming component.

The isolated and potentially washed solid matter is subsequently, potentially after pulverization, dried at temperatures of generally 20-100° C. and with pressures of generally 0.1 mbar to normal pressure (1013 mbar).

A preferred method for isolating DMC catalysts pursuant to the invention from the suspension through filtration, filter cake washing, and drying is described in WO 01/80994 A1.

The concentration of a DMC catalyst used in step a) is 5 to 1000 ppm, preferably 10 to 900 ppm, and particularly preferably 20 to 800 ppm in relation to the quantity of prepolymer bearing hydroxyl groups to be produced. Depending on the requirements profile of the application downstream from the amine addition, the DMC catalyst in the product can be left or (partially) separated. The DMC catalyst can be (partial) separated, for example, by treating with adsorbents. Processes for the separation of DMC catalysts are described, for example, in U.S. Pat. No. 4,987,271 A1, DE 313 22 58 A1, EP 406 440 A1, U.S. Pat. No. 5,391,722 A1, U.S. Pat. No. 5,099,075 A1, U.S. Pat. No. 4,721,818 A1, U.S. Pat. No. 4,877,906 A1, and EP 385 619 A1.

Minimal amounts of an inorganic mineral acid, preferably phosphoric acid, can potentially be added the H functional starter compound prior to bringing it into contact with the DMC catalyst in order to neutralize any traces of alkali in the H functional starter compound.

If the process pursuant to the invention is performed using double metal cyanide catalysts, it is still beneficial to first present the H functional starter compound and the catalyst, to dispense a partial amount of the alkylene oxide compound and potentially other comonomers, and only then to add the unsaturated, cyclical carboxylic acid anhydride. In this manner, a double bond-free polymer structure can first be developed starting with the H functional starter compound. For this reason, all of the aforementioned alkylene oxide compounds or potentially additional comonomers can be used. The unsaturated, cyclical carboxylic acid anhydride is typically added to the reaction mixture then if the aforementioned addition reaction of the alkylene oxide compound to the H functional starter compound is complete.

After the unsaturated, cyclical carboxylic acid anhydride has been added, the alkylene oxide compound is subsequently added again and potentially an additional comonomers. In this regard, the distance between the amine functionality and the hydroxyl group, as previously described, can be set by selecting the substance amounts of alkylene oxide compound(s) in relation to the substance amount of unsaturated, cyclical carboxylic acid anhydride to be added, wherein particularly more than 1 mol of alkylene oxide compound per mol of Zerewitinoff active hydrogen is added. The distance of these two functionalities from each other can also be influenced by adding further comonomers. As mentioned above, carboxylic acid anhydride and—after its abreaction—an additional alkylene oxide compound can be subsequently added again to provide the possibility of integrating more than one amine function per Zerewitinoff active H atom.

Step a) of the method pursuant to the invention will be described in detail according to this variation, wherein the present invention is not limited to the following depiction:

In one embodiment of the process pursuant to the invention, the H functional compound is initially presented with the DMC catalyst in a reactor/reactor system. Minimal amounts of an inorganic mineral acid, preferably phosphoric acid, can potentially be added to the H functional compound prior to bringing it into contact with the DMC catalyst in order to neutralize any traces of alkali in the H functional starter compound or to design the production process in a generally more stable manner.

After heating to temperatures of 50 to 160° C., particularly 60 to 140° C., very particularly preferably 70 to 140° C., the content of the reactor is stripped in a preferred process variation with inert gas over a period of preferably 10 to 60 minutes while stirring. Upon stripping with inert gas, the volatile components are removed by introducing inert gases into the liquid phase with a simultaneously applied vacuum with an absolute pressure of 5 to 500 mbar. After adding typically 5 to 20% by weight of one or more alkylene oxides, potentially already containing a small amount of the unsaturated, cyclical carboxylic acid anhydride and/or additional comonomer, in relation to the amount of the presented H functional compound, the DMC catalyst is activated.

The addition of one or more alkylene oxides and potentially a small amount of the unsaturated, cyclical carboxylic acid anhydride and/or additional comonomers may occur prior to, during or after heating the contents of the reactor to temperatures of 50 to 160° C., preferably 60 to 140° C., very particularly preferably 70 to 140° C.; it occurs preferably after stripping. The activation of the catalyst becomes noticeable through an accelerated decrease of reactor pressure, through which the initial alkylene oxide volume/volume of unsaturated, cyclical carboxylic acid anhydride is shown.

The desired amount of alkylene oxide or alkylene oxide mixture can then be continuously added to the reaction mixture, potentially with the amount of unsaturated, cyclical carboxylic acid anhydride and/or additional comonomers to be dispensed, wherein a reaction temperature of 20 his 200° C., though preferably from 50 to 160° C. is selected. The reaction temperature is identical to the activation temperature in many cases.

Furthermore, an inhibitor, e.g. a phenol derivative, phenothiazine or vitamin E, can be added to the H functional starter compound or reaction mixture prior to adding the unsaturated, cyclical carboxylic acid anhydride.

The catalyst is frequently activated so quickly that dispensing a separate amount of alkylene oxide/unsaturated, cyclical carboxylic acid anhydride for the activation of the catalyst can be omitted and continuous dispensing of the alkylene oxide and unsaturated, cyclical carboxylic acid anhydride can be directly initiated, potentially with a reduced dispense rate at first. The reaction temperature during the alkylene oxide dispensing stage/while the unsaturated, cyclical carboxylic acid anhydride is being dispensed may vary within the described limits. Likewise, the alkylene oxide and unsaturated, cyclical carboxylic acid anhydride may be added to the reactor differently: It is possible to dispense during the gas stage or directly in the liquid stage, e.g. via an immersion tube or a distributor ring located near the bottom of the reactor in a well-mixed area.

In the case of DMC catalyst processes, dispensing during the liquid stage is preferred. The alkylene oxide and unsaturated, cyclical carboxylic acid anhydride should be continuously added to the reactor in such a way that the safety-related pressure limits of the reactor system being used are not exceeded. It is necessary to ensure that sufficient inert gas partial pressure is maintained in the reactor during the start-up and dispensing stage, particularly when codispensing alkylene oxide mixtures containing ethylene oxide or pure ethylene oxide. This can be configured, e.g. through noble gas or nitrogen.

When dispensing during the liquid stage, the dispensing units should be designed to self-empty, for example, by making dispensing holes on the bottom of the distributor ring. A backflow of reaction medium into the dispensing units and reactant templates should generally be prevented through technical measures on the machine. If an alkylene oxide/unsaturated, cyclical carboxylic acid anhydride mixture is dispensed, the respective alkylene oxides and respective unsaturated, cyclical carboxylic acid anhydrides can be added to the reactor separately or as a mixture. A preliminary mixture of alkylene oxides among each other and with the unsaturated, cyclical carboxylic acid anhydride can be achieved, for example, through a mixing unit located in the common dispensing section. Dispensing alkylene oxides and potentially the unsaturated, cyclical carboxylic acid anhydride on the pump discharge side, for example, via pump circulation controlled by heat exchangers, separately or premixed has also been proven positive. For proper mixing with the reaction medium, it is beneficial to integrate a high-shear mixing unit into the alkylene oxide/carboxylic acid anhydride/reaction medium flow. The temperature of an exothermic ring-opening addition reaction is maintained at the desired level through cooling. According to the state of the art regarding the design of polymerization reactors for exothermic reactions (e.g. Ullmann's Encyclopedia of Industrial Chemistry, Vol. B4, pp. 167ff, 5th Ed., 1992), this cooling occurs in general via a reactor wall (e.g. double shell, half-coil pipe) as well as via additional heat exchanger areas situated inside the reactor and/or externally in the pump circulation, e.g. to cooling coils, cooling plugs, panel tube bundle or mixer heat exchangers. They should be configured such that they can provide effective cooling already at the beginning of the dispensing stage, i.e. when filled minimally.

Generally, it is necessary to ensure proper mixing of the reactor contents in all reaction stages through the configuration and use of commercial agitators, wherein particularly single or multi-stage arranged agitators or agitator types operating extensively across the fill level are suitable in this case (see, e.g. the "Apparatuses" manual; Vulkan-Verlag Essen, 1st Edition (1990), pp. 188-208). Particularly technically relevant in this case is a mixing energy introduced in the medium throughout the content of the reactor, which is generally in the range of 0.2 to 5 W/l, with respectively higher local performance levels in the area of the agitator itself and potentially at low fill levels. To achieve optimal agitation, combination of baffles (e.g. flat or tubular baffles) and cooling coils (or cooling plugs) can be arranged in the reactor pursuant to the state of the art, which can extend across the floor of the container. The agitation capacity of the mixing unit may also vary during the dispensing stage depending on the fill level to ensure a particularly high energy input in critical reaction stages. For example, it can be beneficial to mix dispersions containing solid matter, which may be present at the beginning of a reaction, e.g. when using sucrose, particularly intensively.

Additionally, it is necessary to ensure that sufficient dispersion of solid matter in the reaction mixture is guaranteed through the selection of the agitation unit, particularly when using solid H functional starter compounds. In this case, agitation stages on the floor of the reactor as well as agitators suitable in particular for suspending are preferably used. Furthermore, the shape of the agitators should help reduce the foaming of reaction products. The foaming of reaction mixtures can be observed, for example, at the end of the dispensing and subsequent reaction stage if residual epoxides are additionally removed in the vacuum at absolute pressures in the range of 1 to 500 mbar. Agitators that achieve continuous mixing of the liquid surface have proven to be suitable for such cases. Depending on the requirement, the agitator shaft has a floor support and potentially additional support bearings in the container. In this regard, the agitator shaft can be driven from above or from below (with the shaft arranged centrically or eccentrically).

Alternatively, it is also possible to achieve the necessary mixing exclusively by means of pump circulation controlled by a heat exchanger or to operate it as an additional mixing component aside from the agitator unit, wherein the reaction content is transferred as needed (typically 1 to 50 times per hour).

Various reactor types are suitable for conducting the production process pursuant to the invention. Cylindrical containers having a height to diameter ratio of 1:1 to 10:1 are preferably used. Spherical, torispherical, flat or conical floors can be considered, for example, as reactor floors.

Following completion of the dispensing of alkylene oxide and the unsaturated, cyclical carboxylic acid anhydride, and potentially additional comonomers in step a), a subsequent reaction stage may follow, in which the residual alkylene oxide/unsaturated, cyclical carboxylic acid anhydride/additional comonomers is reacted off. The subsequent reaction stage is completed if a decrease in pressure in the reaction tank can no longer be determined. Traces of unreacted alkylene oxides/unsaturated, cyclical carboxylic acid anhydrides can quantitatively be removed after the reaction stage potentially in a vacuum at an absolute pressure of 1 to 500 mbar or through stripping. Stripping removes volatile components, such as (residual) alkylene oxides by introducing inert gas or water vapor in the liquid stage with a simultaneously applied vacuum (for example, by transmitting inert gas at an absolute pressure of 5 to 500 mbar). Removing volatile components, such as unreacted epoxides, can occur in a vacuum or through stripping at temperatures of 20 to 200° C., preferably 50 to 160° C. and preferably while stirring. These stripping processes may also be conducted in so-called stripping columns, in which a flow of inert gas or water vapor is transferred in the opposite direction. Stripping is preferably done with inert gas in the presence of water vapor. After achieving a consistent pressure or after removing volatile components through vacuuming and/or stripping, the product can be released from the reactor.

In the case of variation A) of the first process alternative of step a), the cyclical carboxylic acid anhydride can be dispensed in such a manner that dispensing alkylene oxide/additional comonomers is interrupted and, potentially after a subsequent reaction stage, the unsaturated, cyclical carboxylic acid anhydride is added to the reactor and the dispensing of alkylene oxide/additional comonomers is restarted after adding the desire amount of unsaturated, cyclical carboxylic acid anhydride. Naturally, this process can be repeated multiple times during a reaction sequence. It is particularly preferred that the subsequent alkylene oxide block comprises a quantity of more than 1 mol of alkylene oxide per mol of active H atoms from the H functional compounds used as starter compounds.

It is likewise possible to continuously or gradually vary the ratio of dispensing speeds of alkylene oxide and the dispensing of unsaturated, cyclical carboxylic acid anhydrides in an opposing manner while simultaneously adding both of these components, in which, for example, the ratio of the dispensing flow of unsaturated, cyclical carboxylic acid anhydride increases to that of the alkylene oxide/alkylene oxides assumes values of 0:1 to 1:0.

One characteristic of DMC catalysts is their distinctive sensitivity to high concentrations of hydroxyl groups, which, for example, are caused by large amounts of starters, such as ethylene glycol, propylene glycol, glycerin, trimethylolpropane, sorbitol or sucrose, and polar impurities of the reaction mixture or the starter(s). The DMC catalysts may not then be transferred to the polymerization active form during the reaction initiation stage. Impurities can be, e.g. water or compounds with a high number of hydroxyl groups situated in close proximity, such as carbohydrates and carbohydrate derivatives. Substances with carbonyl groups situated in close proximity or those close to hydroxyl groups have a negative effect on the activity of catalysts.

To enable starters with high concentrations of OH groups or starters with contaminants that are perceived as catalyst toxins to still undergo DMC catalyzed alkylene oxide addition reactions, the hydroxyl group concentration should be reduced or the catalyst toxins should be rendered harmless. In this regard, prepolymers can first be produced from these starter compounds by means of a basic catalyst, which are then transferred to the desired alkylene oxide addition products of high molar masses after processing by means of DMC catalysis. For example, the aforementioned "prefabricated alkylene oxide addition products" suitable as starters fall under these prepolymers. The disadvantage with these approaches is that these prepolymers often obtained by means of basic catalysis have to be processed very carefully to preclude the deactivation of the DMC catalyst through basic catalyst traces introduced via prepolymers.

This disadvantage can be overcome through the so-called process of continuous starter dispensing. In this regard, critical starter compounds are not presented in the reactor, but rather are continuously added to the reactor in addition to alkylene oxides during the reaction. Prepolymers may be presented in this process as starter medium for the reaction and small amounts of the product itself can also be used as starter medium. Thus, the necessity of first having to separately produce prepolymers suitable for further alkylene oxide additions is eliminated.

In variation B) of the first process alternative of step a) pursuant to the invention, therefore, a starter polyols and the DMC catalyst are presented in the reaction system and the H functional compound is continuously added with the alkylene oxide and unsaturated, cyclical carboxylic acid anhydride. Alkylene oxide addition products, such as polyether polyols, polyester polyols, polyether-ester polyols, polycarbonate polyols, polyester carbonate polyols, polyether carbonate polyols are respectively suitable as starter polyols in step a), for example, with OH values in the range of 3 to 1000 mg KOH/g, preferably from 3 to 300 mg KOH/g, and/or an intermediate product produced separately pursuant to step a). An intermediate product produced separately pursuant to step a) is preferably used as a starter polyols in step a).

In a less preferred variation of this embodiment B), it is likewise possible to continuously or gradually vary the ratio of dispensing speeds of alkylene oxide and the dispensing of unsaturated, cyclical carboxylic acid anhydrides in an opposing manner during the addition stage of the three components, in which, for example, the ratio of the dispensing flow of unsaturated, cyclical carboxylic acid anhydride increases to that of the alkylene oxide/epoxide assumes values of 0:1 to 1:0. This embodiment is less preferred as according to it, the intermediate product pursuant to step a) is obtained in a less consistent form.

In embodiment B) of the first process alternative of step a), dispensing of the H functional compound and alkylene oxide as well as the unsaturated, cyclical carboxylic acid anhydride is preferably simultaneously completed, or the H functional compound and a first partial amount of alkylene oxide and a first partial amount of carboxylic acid anhydride is initially added together and subsequently the second partial amount of alkylene oxide and unsaturated, cyclical carboxylic acid anhydride is added, wherein the sums of the first and second partial amount of alkylene oxide and that of the unsaturated, cyclical carboxylic acid anhydride corresponds to the total amount of the quantity of one or more alkylene oxides or of one or more unsaturated, cyclical carboxylic acid anhydrides used in step a). The first partial amount is preferably 60 to 98% by weight and the second partial amount is 40 to 2% by weight of the overall amount of alkylene oxide to be dispensed in step a). The first partial amount is preferably 0 to 100% by weight and the second partial amount is 100 to 0% by weight of the overall amount of one or more unsaturated, cyclical carboxylic acid anhydrides to be dispensed in step a).

If the composition of the alkylene oxides and/or the composition/dispensing rate of one or more unsaturated, cyclical carboxylic acid anhydrides is modified after dispensing of the H functional compound is concluded, products with multi-block structures can also be produced pursuant to process variation B). It is preferable with process variation B) as well that dispensing of unsaturated, cyclical carboxylic acid anhydride is concluded prior to dispensing alkylene oxide, particularly preferably in such a way that this concluding alkylene oxide block comprises a quantity of more than 1 mol of alkylene oxide per mol of active H atoms from the H functional compounds used as starter compounds. After adding the reagents, a subsequent reaction stage may follow, in which the use of alkylene oxide/unsaturated, cyclical carboxylic acid anhydride can be quantified by monitoring the pressure. After achieving a constant pressure, the final product may be released, potentially after attaching a vacuum or through stripping to remove non-reacted alkylene oxides, as described above.

In variation C) of the first process alternative from step a) of the process pursuant to the invention, the prepolymer containing double bonds can be continuously produced. In this regard, the DMC catalyst is continuously added to the reactor or a reactor system under alkoxylation conditions in addition to alkylene oxide and the H functional compound as well as unsaturated, cyclical carboxylic acid anhydride, and the product is continuously removed from the reactor or reactor system after a preselected average retention time. In the case of process variation C), it is preferable that a reactor cascade is used as a reactor system, for which a third, continuously operated reactor is located between the secondary reactor and the actual reactor, in which exclusively one or more alkylene oxides are continuously dispensed. In a particularly preferred embodiment of process variation C), this concluding alkylene oxide block comprises a quantity of more than 1 mol of alkylene oxide per mol of active H atoms from the H functional compounds used as starter compounds.

Continuous subsequent reaction stages may follow, for example in a reactor cascade or in a tube reactor. Volatile components can be removed in a vacuum and/or through stripping, as described above.

The OH values of unsaturated polyether-ester polyols obtainable pursuant to the first process alternative of step a) preferably have values of 3 mg KOH/g to 200 mg KOH/g, particularly preferably from 10 to 60 mg KOH/g, and very particularly preferably from 20 to 50 mg KOH/g.

The OH value can be determined, e.g. titrimetrically according to regulation DIN 53240 or spectroscopically via NIR.

Equivalent molar mass refers to the overall mass of the material containing active hydrogen atoms divided by the number of active hydrogen atoms. In the case of materials containing hydroxy groups, it relates to the OH value as follows:

$$\text{Equivalent molar mass} = 56100/\text{OH value [mg KOH/g]}$$

Anti-aging agents can potentially be added to the intermediate products available according to step a) of the process pursuant to the invention, e.g. antioxidants.

Step a), Second Process Alternative:

According to a second alternative process, the H functional starter compound may first be reacted with the unsaturated, cyclical carboxylic acid anhydride and subsequently with the alkylene oxide compound or the H functional starter compound simultaneously with the unsaturated, cyclical carboxylic acid anhydride and alkylene oxide compound. This variation is preferred, for example, if the H functional starter compound has a number average molar mass from 200 to 20000 g/mol, preferably from 600 to 10000 g/mol.

The indirect process product does not necessarily have to be cleaned for this process prior to subsequent use, for example, for the production of polyurea/polyurethane or polyurethane-urea polymers. The process products have a high purity, particularly with regard to the share of undesired transesterification products and a comparably high number of amine and hydroxy groups.

The process according to this second alternative may still be configured in such a way that unsaturated, cyclical carboxylic acid anhydride is added again following abreaction of the present alkylene oxide compound, for example, approx. 1 mol of carboxylic acid anhydride per mol of OH groups formed through the addition of the alkylene oxide compound. In other words, process step a) is repeated, wherein the H functional starter compound bearing a Zerewitinoff active H atom is now the addition production from the original starter compound, cyclical, unsaturated carboxylic acid anhydride, and alkylene oxide compound. Subsequently, a desired amount of alkylene oxide compound is added again to obtain the prepolymer bearing hydroxyl groups. This has then two double bonds per hydroxyl group, such that two amine functionalities can later be introduced via Michael addition. The aforementioned reaction can be repeated two or more times as well, such that a desired number of amine functionalities per original Zerewitinoff active H atom can be integrated into the hydroxy amino polymer. This can be, for example, 2 or more, particularly 3 or more amine functionalities per original Zerewitinoff active H atom.

In the case of the second process alternative, it is further preferred that this is conducted through the use of an amine catalyst, which is preferably selected from tertiary amines. In the case of the hydroxy amino polymers obtained in the process, the distance between the amine functionality and the hydroxyl group in normally 6 or 7 bond lengths. The reason for this lies in the fact that normally only one alkylene oxide compound can be linked to a carboxylic acid group due to amine catalysis. Otherwise, there is a risk of saponification of the already established ester functionality or a risk of transesterification. The amine catalyst is particularly selected from the group comprising:

(A1) Amines of a General Formula (2):

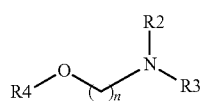

(2)

wherein the following applies:
R2 and R3 are independently hydrogen, alkyl or aryl; or
R2 and R3 form an aliphatic, unsaturated or aromatic heterocycle together with the
N atom bearing them;
n is a whole number from 1 to 10;
R4 is hydrogen, alkyl or aryl; or
R4 represents —$(CH_2)_x$—N(R41)(R42), wherein the following applies:
R41 and R42 are independently hydrogen, alkyl or aryl; or
R41 and R42 form an aliphatic, unsaturated or aromatic heterocycle together with the nitrogen atom bearing them;
x is a whole number from 1 to 10;
(B1) Amines of a General Formula (3):

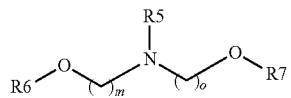

(3)

wherein the following applies:
R5 is hydrogen, alkyl or aryl;
R6 and R7 are independently hydrogen, alkyl or aryl;
m and n are independently a whole number from 1 to 10; and/or:
(C1) Diazabicyclo [2.2.2]octane, diazabicyclo[5.4.0]undec-7-ene, di al kylbenzyl amine, dimethylpiperazine, 2,2'-Dimorpholinyldiethylether and/or pyridine.

Amines of said general formula (2) can be described in the broadest sense as amino alcohols or their ethers. If R4 is hydrogen, the catalysts can be integrated in a polyurethane matrix if the hydroxy amino polymer pursuant to the invention is reacted with a polyisocynate. This is beneficial in preventing the discharge of the catalyst, which, in the case of amines, can be linked to negative odor problems, on the polyurethane surface—so called "fogging" or VOC (volatile organic compounds) problem.

Amines of said general formula (3) can be described in the broadest sense as amino (bis) alcohols or their ethers. If R6 and/or R7 hydrogen, these catalysts can likewise be integrated in a polyurethane matrix.

In this context, it is preferable that R2 and R3 are methyl, R4 is hydrogen, and n=2 or R2 and R3 are methyl, R4 is —$(CH_2)_2$—$N(CH_3)_2$, and n=2 in the amine of the general formula (2). Overall, either N,N-dimethylethanolamine or bis(2-(dimethylamino)ethyl)ether emerges.

Furthermore, it is preferable that R5 is methyl, R6 and R7 are hydrogen, m=2, and o=2 in the amine of the general formula (3). Overall, N-methyldiethanolamine emerges.

Particularly preferred catalysts are diazabicyclooctane, N-methyldiethanolamine, dimethylethanolamine, bis(2-(dimethylamino)ethyl)ether, diazabicyclo[5.4.0]undec-7-ene, dialkylbenzylamine, dimethylpiperazine, 2,2'-dimorpholinyldiethylether, and pyridine or combinations thereof.

The amine-catalyzed process alternative is not limited to the use of the aforementioned catalysts; however, it has been proven that certain amines may have a negative impact on the purity of the reaction product. This can be revealed by the fact that a partial division of the ester bonds of the unsaturated carboxylic acid, i.e. a saponification, may occur or may lead to undesired transesterification reactions. The byproducts are partially difficult to remove or worsen the homogeneity of the reaction product if they are not removed or cannot be removed. For this reason, the catalyst should not be imidazole or N-methylimidazole, as these catalysts may lead to the aforementioned undesired secondary reactions. In other words, these compounds should not be brought into contact with the reactants or (intermediate) products throughout the entire reaction sequence.

With regard to the time the catalyst was added, it is beneficial if the catalyst is added simultaneously or prior to adding the unsaturated, cyclical carboxylic acid anhydride.

According to a particularly preferred embodiment of this process, the amine catalyst is added to the reaction mixture simultaneously or prior to the reaction of the prepolymer bearing carboxyl groups with the alkylene oxide compound. The amount of the catalyst with regard to the overall mass of the reaction sequence can be, for example, ≥10 ppm to ≤10000 ppm, preferably ≥50 ppm to ≤5000 ppm, and more preferably ≥100 ppm to ≤2000 ppm.

Step b) of the process pursuant to the invention is described in detail in the following. Even this depiction is purely an example and cannot be considered as limiting the present invention:

For step b), a suitable amine is introduced to the reaction at temperatures of 0° C. to 150° C., preferably 10° C. to 100° C., and particularly preferably 20° C. to 80° C. with products from step a). The molar ratio of primary amino groups to addition-capable double bonds is, for example, approx. 1:1 to 1.1:1. Although the reaction can be catalyzed with copper acetate, tin chloride or acetic acid, it is preferably performed without the addition of a catalyst.

In general, the amines under inert gas are added to the presented intermediate products from step a) and stirred for a period of 1 hour to approx. 48 hours at the specified temperatures.

Pre-mixing the amines with the intermediate product from step a) is likewise possible, for example, using a mixing unit located in the collective dispensing section ("inline blending").

The reaction progress can be quantified via conventional methods such as gas chromatographic inspections performed online or offline or spectrographic methods such as NMR or IR spectroscopy. Traces of unreacted amines or possible surpluses of amine can be quantitatively removed after the reaction stage potentially in a vacuum at an absolute pressure of 1 to 500 mbar or through stripping.

The reaction of a component obtained via the first process alternative from step a) with the amine(s) in step b) may occur in principal in the same reactor as the production of the component pursuant to step a). However, it is preferable in this case that the reaction pursuant to step b) be performed in another reactor as residual traces of amine in the reactor may prevent conducting the next DMC catalyzed step a).

Hydroxy Amino Polymer:

As already explained above, the present invention relates to a hydroxy amino polymer as well, which is can be achieved according to the process pursuant to the invention.

In a beneficial configuration of the hydroxy amino polymer pursuant to the invention, it comprises polyester polyol units, polyester-polyether polyol units and/or polyether polyol units, particularly polyester-polyether polyols units and/or polyether polyol units with a share of oxyethylene units of 40 to 90% by weight.

According to a particularly preferable embodiment of the hydroxy amino polymer pursuant to the invention, it has the general formula (I)

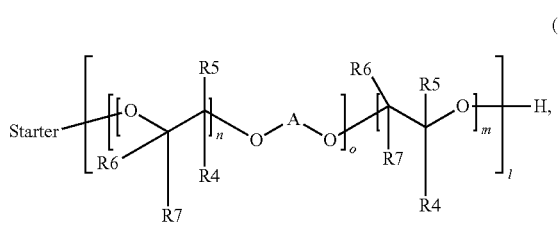

wherein
"starter" represents the radical of the H functional starter compound,
A represents an aspartate group of the following structure of formulas (IIa) or (IIb)

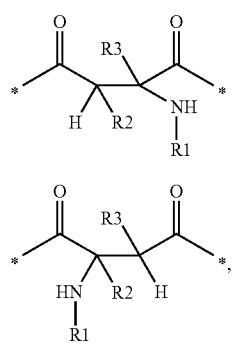

in which
R1 represents hydrogen or an aliphatic, cycloaliphatic or aromatic radical, which may also contain heteroatoms, particularly nitrogen atoms or oxygen atoms as well as hydroxyl groups,
R2 and R3 independently represent hydrogen or an aliphatic or aromatic radical and
R2 and R3 may also be a component of a cycloaliphatic ring system,
R4, R5, R6, and R7 independently represent hydrogen or an aliphatic or aromatic radical and R5 and R6 may also be a component of a cycloaliphatic ring system, l corresponds to the number of Zerewitinoff active hydrogen atoms of the H functional starter compound,
m, n, and o are independently whole numbers, wherein n, o=0 or ≥1 and m≥1, and
n, m are preferably 1 to 430, particularly 2 to 430, preferably 4 to 430, o is preferably 1 to 100, particularly 1 to 50 and preferably 1 to 10, and the ratio of o to 1 in the medium is at least 0.6
and wherein the equivalent molar mass of the structure shown in formula I does not exceed the value of 18900 g/mol.

Polyurea/Polyurethane System:

A further object of the invention relates to a polyurea/polyurethane system comprising isocyanate functional prepolymers as a component A) can be achieved through a reaction of
aliphatic and/or aromatic polyisocyanates A1) with
polyols A2), which may in particular have a number average molecular weight of ≥400 g/mol and an average OH functionality of 2 to 6,
a hydroxy amino polymer pursuant to the invention as a component B),
potentially organic fillers, which may in particular have a viscosity measured according to DIN 53019 at 23° C. in the range of 10 to 6000 mPa, as a component C),
reaction products of isocyanate functional prepolymers according to component A) with hydroxy amino functional compounds according to component B), and/or organic fullers according to component C) potentially as component D), and
potentially water and/or a tertiary amine as a component E).

Polyurea/polyurethane systems pursuant to the invention are achieved by mixing prepolymers A) with the hydroxy amino functional compound B) as well as potentially the components C), D), and/or E). In this regard, the ratio of free or blocked amino groups to free NCO groups is preferably 1:1.5, particularly preferably 1:1. Water and/or amine are added to component B) or C) in the process.

Isocyanate functional prepolymers A) can be achieved through a reaction of polyisocyanates A1) with polyols A2) potentially using catalysts and secondary and additional substances.

Monomeric, aliphatic or cycloaliphatic di or triisocyanates, such as 1,4-butylene diisocyanate (BDI), 1,6-hexamethylene diisocyanate (HDI), isophorone diisocyanate (IPDI), 2,2,4- and/or 2,4,4-trimethylhexamethylendiisocyanat, the isomeric bis-(4,4'-isocyanatocyclohexyl)-methane or its mixtures of any isomeric content, 1,4-cyclohexylene diisocyanate, 4-isocyanatomethyl-1,8-octane diisocyanate (nonane triisocyanate), as well as alkyl-2,6-diisocyanatohexanoate (lysine diisocyanate) with C1-C8 alkyl groups, can be used as polyisocyanates A1).

In addition to the aforementioned monomeric polyisocyanates A1), their higher molecular derived products may also be used in a uretdione, isocyanurate, urethane, allophanate, biuret, iminooxadiazindione, or oxadiazine trione structure as well as its mixtures.

Polyisocyanates A1) of the aforementioned type are preferably used with exclusively aliphatically or cycloaliphatically bonded isocyanate groups or their mixtures.

It is likewise preferable if polyisocyanates A1) of the aforementioned type are used with an average NCO functionality of 1.5 to 2.5, preferably of 1.6 to 2.4, particularly preferably of 1.7 to 2.3, and very particularly preferably of 1.8 to 2.2, and particularly of 2.

Hexamethylene diisocyanate is very particularly preferably used as a polyisocyanate A1).

One preferred embodiment of the polyurea/polyurethane system pursuant to the invention provides that the polyols A2) are polyester polyols and/or polyester-polyether polyols and/or polyether polyols. In this regard, polyester-polyether polyols and/or polyether polyols with an ethylene oxide share of 40 to 90% by weight are particularly preferable.

It is also preferable if the polyols A2) have a number average molecular weight of 4000 to 8500 g/mol.

Suitable polyether ester polyols are preferably produced according to the state of the art through polycondensation from polycarboxylic acids, anhydrides of polycarboxylic acids, as well as esters of polycarboxylic acids with volatile alcohols, preferably C1 to C6 mono-ols, such as methanol, ethanol, propanol or butanol, with a molar-surplus, low-molecular and/or higher molecular polyol; wherein polyols containing ether groups are potentially used in mixtures with other polyols void of ether groups as a polyol.

Naturally, mixtures of higher molecular and low-molecular polyols may also be used for polyether-ester synthesis.

Such molar-surplus, low-molecular polyols are polyols with molar masses of 62 to 299 Da having 2 to 12 C atoms and hydroxyl functionalities of at least 2, which may also be branched or unbranched and their hydroxyl groups are primary or secondary. These low-molecular polyols may have ether groups as well. Typical substitutes are ethylene glycol, propanediol-1,2, propanediol-1,3, butanediol-1,4, butanediol-2,3, 2-methylpropanediol-1,3, pentanediol-1,5, hexanediol-1,6, 3-methyl pentanediol-1,5, 1,8-octanediol, 1,10-decanediol, 1,12-dodecanediol, cyclohexanediol, diethylene glycol, triethylene glycol, and higher homologs, dipropylene glycol, tripropylene glycol, and higher homologs, glycerin, 1,1,1-Trimethylolpropane, as well as oligo-tetrahydrofurans with hydroxyl end groups. Naturally, mixtures may also be used within these groups.

Molar-surplus higher molecular polyols are polyols with molar masses of 300 to 3000 Da, which can be obtained through ring-opening polymerization of epoxides, preferably ethylene and/or propylene oxide, as well as through acid-catalyzed, ring-opening polymerization of tetrahydrofuran. Either alkali hydroxide or double metal cyanide catalysts are used for ring-opening polymerization of epoxides.

All at least bifunctional molecules from the group of amines and the aforementioned low-molecular polyols can be used as starter for ring-opening epoxide polymerization. Typical substitutes are 1,1,1-Trimethylolpropane, glycerin, o-TDA, ethylenediamine, propylene glycol-1,2, etc. as well as water, including their mixtures. Naturally, mixtures may also be used within this group of surplus higher molecular polyols.

The structuring of higher molecular polyols, if referring to hydroxyl group-terminated polyalkylene oxides from ethylene and/or propylene oxide, can occur statistically or in blocks, wherein mix blocks may also be contained.

Polycarboxylic acids are both aliphatic and aromatic carboxylic acids, which may be cyclical, linear, branched or unbranched and may have between 4 and 24 C atoms.

Examples are succinic acid, glutaric acid, adipic acid, azelaic acid, sebacic acid, 1,10-decanedicarboxylic acid, 1,12-dodecandicarboxylic acid, phthalic acid, terephthalic acid, isophthalic acid, trimellitic acid, pyromellitic acid. Succinic acid, glutaric acid, adipic acid, sebacic acid, lactic acid, phthalic acid, terephthalic acid, isophthalic acid, trimellitic acid, and pyromellitic acid are preferable. Succinic acid, glutaric acid, and adipic acid are particularly preferable.

Furthermore, the group of polycarboxylic acids also comprises hydrocarboxylic acids or their lactones, such as caprolactone, lactic acid, hydroxybutyric acid, ricinoleic acid, etc. This also includes monocarboxylic acids, particularly those having more than 10 C atoms, such as soy oil fatty acids, palm oil fatty acids, and peanut oil fatty acids, wherein their share of the overall reaction mixture forming the polyether-ester polyol does not exceed 10% by weight and, in addition, the resulting decreased functionality is compensated through the use of at least trifunctional polyols, whether on the part of low-molecular or higher molecular polyols.

Polyether-ester polyols are produced according to the state of the art at an elevated temperature in the range of 120 to 250° C. initially at normal pressure and subsequently by attaching a vacuum from 1 to 100 mbar, preferably, though not necessarily, through the use of a esterification or transesterification catalyst, wherein the reaction is completed to the extent that the acid value decreases to 0.05 to 10 mg KOH/g, preferably 0.1 to 3 mg KOH/g, and particularly preferably 0.15 to 2.5 mg KOH/g.

Furthermore, an inert gas can be used within the scope of a normal pressure stage prior to attaching a vacuum. Naturally, liquid or gaseous entrainers can be used alternatively or for individual stages of esterification. For example, the reaction water can be discharged using nitrogen as a carrier gas just as by using an azeotropic entrainer, such as benzole, toluene, xylol, dioxane, etc.

Naturally, mixtures of polyether polyols can be used with polyester polyols at any ratio.

Polyether polyols are preferably polyalkylene oxide polyethers based on ethylene oxide and potentially propylene oxide.

These polyether polyols are preferably based on di, tri or higher functional starter molecules, such as di, tri or higher functional polyols or amines.

Examples of such starters are water (regarded as a diol), ethylene glycol, propylene glycol, butylene glycol, glycerin, TMP, sorbitol, pentaerythritol, triethanolamine, ammonia or ethylene diamine.

Polycarbonates having hydroxyl groups, preferably polycarbonate diols, can likewise be used with number average molecular weights of 400 to 8000 g/mol, preferably 600 to 3000 g/mol. These can be achieved through a reaction of carbonic acid derivatives, such as diphenyl carbonate, dimethyl carbonate or phosgene, with polyols, preferably diols.

Examples of these types of diols are ethylene glycol, 1,2- and 1,3-propanediol, 1,3- and 1,4-butanediol, 1,6-hexanediol, 1,8-octanediol, neopentyl glycol, 1,4-bishydroxymethyl cyclohexane, 2-methyl-1,3-propanediol, 2,2,4-trimethylpentanediol-1,3, dipropylene glycol, polypropylene glycols, dibutylene glycol, polybutylene glycols, bisphenol A and lactone-modified diols of the aforementioned type.

A trifunctional polyol is particularly preferably used for the production of component A, particularly a glycerin-started polyether.

The polyisocynate A1) may be reacted with polyol A2) at an NCO/OH ratio of preferably 4:1 to 12:1, particularly preferably 8:1 for the production of prepolymer A), and subsequently the share of non-reacted polyisocyanate can be separated using suitable methods. Thin film distillation is usually used in this case, wherein prepolymers having residual monomer contents of less than 1% by weight, preferably less than 0.1% by weight, and particularly preferably less than 0.03% by weight can be achieved.

Stabilizers, such as benzoyl chloride, isophthaloyl chloride, dibutyl phosphate, 3-Chloropropionic acid or methyl tosylate, can potentially be used during production.

The reaction temperature when producing prepolymers A) is preferably 20 to 120° C., and more preferably 60 to 100° C.

The produced prepolymers have an average NCO content measured according to DIN EN ISO 11909 of 2 to 10% by weight, preferably 2.5 to 8% by weight.

According to a further embodiment of the polyurea/polyurethane system pursuant to the invention, prepolymers A) may have an average NCO functionality of 1.5 to 6, preferably 1.6 to 4.5, more preferably 1.7 to 4, particularly preferably 1.8 to 3.5, and particularly 3.

Organic fillers of component C) may preferably be hydroxy functional compounds, particularly polyether polyols with repetitive ethylene oxide units.

It is beneficial if the fillers of component C) have an average OH functionality of 1.5 to 3, preferably 1.8 to 2.2, and particularly preferably 2.

For example, liquid polyethylene glycols, such as PEG 200 to PEG 600, their mono or dialkyl ethers, such as PEG 500 dimethyl ethers, liquid polyethers and polyester polyols, liquid polyesters, such as Ultramoll (Lanxess A G, Leverkusen, Del.) as well as glycerin and its liquid derivatives, such as triacetine (Lanxess A G, Leverkusen, Del.), can be used as organic fillers at 23° C.

The viscosity of the organic fillers—measured according to DIN 53019 at 23° C.—is preferably 50 to 4000 mPa, particularly preferably 50 to 2000 mPa.

In a preferred embodiment of the polyurea/polyurethane system pursuant to the invention, polyethylene glycols are used as organic fillers. They preferably have a number average molecular weight of 100 to 1000 g/mol, particularly preferably 200 to 400 g/mol.

To further reduce the average equivalent weight of the compound used overall for prepolymer grouping in relation to NCO reactive groups, it is possible to additionally produce reaction products of prepolymers A) with the amino functional compound B) and/or the organic fillers C)—if they are amino or hydroxy functional—in a separate preliminary reaction and to then use them as a higher molecular hardening component.

Ratios of isocyanate reactive groups to isocyanate groups of 50 to 1 to 1.5 to 1, particularly preferably 15 to 1 to 4 to 1 are preferably used in the preliminary extension.

The benefit of this modification through preliminary extension is that the equivalent weight and equivalent volume of the hardening component can be modified to greater extents. Thus, commercially available 2-chamber dispensing systems can be used for the application to achieve an adhesive system that can be added at existing ratios to the chamber volumes in the desired ratio of NCO reactive groups to NCO groups.

A further preferred embodiment of the polyurea/polyurethane system pursuant to the invention provides that the component E) contains a tertiary amine of a general formula (IX),

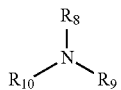

(IX)

in which $R_8$, $R_9$, $R_{10}$ may independently be alkyl or heteroalkyl radicals with heteroatoms in the alkyl chain or at their ends, or $R_8$ and $R_9$ can form an aliphatic, unsaturated or aromatic heterocycle together with the nitrogen atom bearing them, which can potentially contain additional heteroatoms.

These polyurea/polyurethane systems are distinguished by a particularly rapid hardening.

The compounds used in component E) can particularly preferably be tertiary amines selected from the group of triethanolamine, tetrakis (2-hydroxyethyl) ethylenediamine, N,N-dimethyl-2-(4-methylpiperazine-1-yl)ethanamine, 2-{[2-(dimethylamino)ethyl](methyl)amino}ethanol, 3,3',3''-(1,3,5-triazinan-1,3,5-triyl)tris(N,N-dimethyl-propane-1-amine).

Very particularly high hardening speeds can also be achieved if component E) contains 0.2 to 2.0% by weight of water and/or 0.1 to 1.0% by weight of tertiary amine.

According to a particularly preferred embodiment of the polyurea/polyurethane system pursuant to the invention, the reaction product of components A1 and A2 corresponds to a trifunctional isocyanate of a general formula (X)

(X)

particularly of a general formula (XI),

(XI)

wherein X in formula (X) represents an n or, in formula (XI), a trivalent organic radical, such as a glycerin radical, and $R_{11}$, $R_{12}$ and $R_{13}$ independently represent equal or different organic radicals without a Zerewitinoff active H atom. Radical $R_{11}$, $R_{12}$, and $R_{13}$ preferably contain oxyalkylene units or are comprised thereof. In this context, it is further preferable if the oxyalkylene units have a share of oxyethylene units of 40 to 90% by weight. The remaining oxyalkylene units are particularly formed through oxypropylene units.

Naturally, pharmacologically active substances, such as analgesics with or without an anti-inflammatory effect, antiphlogistic, antimicrobially active substances, antimycotics, and antiparasitically active substances can be integrated in the polyurea/polyurethane systems as well.

The active substances may be pure active substances or in the form of a capsule to achieve, for example, a time-delayed release. Within the scope of the present invention, a number of types and classes of active substances can be used as medically active substances.

One such medically active substance may comprise, for example, a component releasing nitrogen monoxide under in vivo conditions, preferably L-arginine or a component containing or releasing L-arginine, particularly preferably L-arginine hydrochloride. Proline, ornithine and/or other biogenic intermediate stages, such as biogenic polyamines (spermine, spermidine, putrescine, or bioactive artificial polyamines) may be used as well. As we know, these types of components promote the healing of wounds, wherein their continuous quantitatively nearly equal release is particularly tolerable for healing wounds.

Additional active substances usable pursuant to the invention comprise at least one substance selected from the group of vitamins or provitamins, carotinoides, analgesics, antiseptics, hemostyptics, antihistamines, antimicrobial metals or their salts, substances promoting the herbal healing of wounds or substance mixtures, herbal extracts, enzymes, growth factors, enzyme inhibitors as well as combinations thereof.

Particularly non-steroid analgesics, especially salicylic acid, acetylsalicylic acid and their derivatives, e.g. Aspirin®, aniline and its derivatives, acetaminophen e.g. Paracetamol®, anthranilic acid and its derivatives, e.g. mefenamine acid, pyrazole or its derivatives, methamizole, Novalgin®, phenazone, Antipyrin®, isopropylphenazone, and very particularly preferably aryl acetic acid, as well as its derivatives, heteroaryl acetic acids and its derivatives, arylpropionic acids and its derivatives, and heteroaryl propionic acids and its derivatives, e.g. Indometacin®, Diclophenac®, Ibuprofen®, Naxoprophen®, Indomethacin®, Ketoprofen®, Piroxicam® are suitable as analgesics.

As growth factors, the following should be mentioned in particular: aFGF (Acidic Fibroplast Growth Factor), EGF (Epidermal) Growth Factor), PDGF (Platelet Derived Growth Factor), rhPDGF-BB (Becaplermin), PDECGF (Platelet Derived Endothelial Cell Growth Factor), bFGF (Basic Fibroplast Growth Factor), TGF α; (Transforming Growth Factor alpha), TGF β (Transforming Growth Factor beta), KGF (Keratinocyte Growth Factor), IGF1/IGF2 (Insulin-Like Growth Factor), and TNF (Tumor Necrosis Factor).

Particularly those fat-soluble or water soluble vitamins, vitamin A, group of retinoids, provitamin A, group of carotenoids, particularly β-carotene, vitamin E, group of tocopherols, particularly α-Tocopherol, β-Tocopherol, γ-Tocopherol, δ-Tocopherol, and α-Tocotrienol, β-Tocotrienol, γ-Tocotrienol, and δ-Tocotrienol, vitamin K, phylloquinone, particularly phytomenadione or herbal vitamin K, vitamin C, L-ascorbic acid, vitamin B 1, thiamin, vitamin B2, riboflavin, vitamin G, vitamin B3, niacin, nicotinic acid, and nicotinic acid amide, vitamin B5, pantothenic acid, provitamin B5, panthenol or dexpanthenol, vitamin B6, vitamin B7, vitamin H, biotin, vitamin B9, folic acid as well as combinations thereof are suitable as vitamins or provitamins.

As an antiseptic, it is necessary to use a medium that works as a germicide, bactericide, bacteriostatic, fungicide, virucide, virustatic, and/or general microbiocide.

Particularly those substances that are selected from the group of resorcinol, iodine, iodine povidone, chlorhexidine, benzalkonium chloride, benzoic acid, benzoyl peroxide or cethylpyridiniumchloride are suitable. Moreover, particularly antimicrobial metals can be used as antiseptics. Particularly silver, copper or zinc, as well as their salts, oxides or complexes can be used together or independently as antimicrobial metals.

In conjunction with the present invention, particularly chamomile extracts, hamamelis extracts, e.g. Hamamelis virginiana, calendula extract, aloe extract, e.g. Aloe vera, Aloe barbadensis, Aloe ferox or Aloe vulgaris, green tea extracts, seaweed extract, e.g. red algae or green algae extract, avocado extract, myrrh extract, e.g. Commophora molmol, bamboo extracts as well as combinations thereof are referred to as herbal active substances promoting the healing of wounds.

The content of the active substances is primarily aligned with the medically necessary dose as well as tolerability with the remaining components of the composition pursuant to the invention.

The polyurea/polyurethane system pursuant to the invention is particularly suited to close, bond, adhere or cover cell tissue and particularly for stopping the discharge of blood or tissue fluids or closing leakages in cell tissue. It can be particularly preferably used for the application or production of a medium for closing, bonding, adhering or covering human or animal cell tissue. It can help to produce adhesive joints that are quick-hardening, strongly bonded to tissue, transparent, flexible, and bio-compatible.

Another object of the invention is a dispensing system with two chambers for a polyurea/polyurethane system pursuant to the invention, for which component A) is contained in one chamber, component B) and potentially components C), D), and E) of the polyurea/polyurethane system in another chamber. Such a dispensing system is particularly suitable for applying the polyurea/polyurethane system as an adhesive to tissue.

The present invention will be explained in further detail in the following using embodiment examples.

Methods for Measurement and Determination:

Molar masses: The molar masses were determined as follows using gel permeation chromatography (GPC): Calibration was performed with polystyrene standards with molar masses of Mp 1,000,000 to 162. Tetrahydrofuran p.A. was used as eluent. The following parameters were maintained during the double measurement: Degassing: Online— degasser; Flow rate: 1 ml/min.; Analysis period: 45 minutes; detectors: refractometer and UV detector; injection volume: 100 µl-200 µl. The calculation of the molar mass average values Mw, Mn, and Mp as well as polydispersity Mw/Mn was performed using software. Baseline points and evaluation limits were defined according to DIN 55672 Part 1.

The OH values were determined according to the regulation of DIN 53240.

The acid figures were determined according to the regulation of DIN EN ISO 2114.

NCO content: If not otherwise expressly stated, volumetrically determined according to DIN-EN ISO 11909.

Viscosity: Was determined according to ISO 3219 at 23° C.

Residual monomer content: Determined according to DIN ISO 17025

Substances:

HDI: Hexamethylene diisocyanate (Bayer MaterialScience AG)

Insofar as not otherwise stated, the used chemicals were purchased from Aldrich or Acros.

Producing Hydroxy Amino Polymers

EXAMPLE 1: PRODUCING A TRIFUNCTIONAL HYDROXY AMINO POLYMER 650 g (0.146 mol) of a trifunctional, glycerin-started polyether polyol were presented in a 1 l laboratory autoclave in a nitrogen atmosphere with an ethylene oxide/propylene oxide ratio of 73/27 (w/w) and OH value=37.9 mg KOH/g (molar mass 4440 g/mol) and then heated to 60° C. At this temperature, 41.8 g (0.426 mol) of maleic acid anhydride and 0.73 g of N-methyldiethanolamine were added and then stirred for 60 minutes at 60° C. Subsequently, it was heated to 90° C.; 77.4 g (1.756 mol) of ethylene oxide were dispensed in the autoclaves at this temperature within 30 minutes and then subsequently reacted at this temperature for 5 hours. Volatile components were baked out in the vacuum at 90° C. for 60 minutes and the reaction was then cooled to room temperature.

A preliminary product is obtained having an OH value of 35.5 mg KOH/g and an acid value of 0.12 mg KOH/g.

Michael Addition of Pentylamine:

0.65 g (3 equivalents) of pentylamine was added to 11.85 g of the preliminary product. The reaction mixture was stirred for 6 hours at 60° C. in the heating block. Potentially surplus amine was then removed in the high-vacuum.

The following amines were reacted nnalogouslv:

TABLE 1

| Amine for Michael addition | Weight of the amine sample | Hydroxy amino polymer |
|---|---|---|
| N-pentylamine | 0.63 g | 2 |
| N-propylamine | 0.44 g | 3 |
| N-butylamine | 0.54 g | 4 |
| N-hexylamine | 0.76 g | 5 |
| N-decylamine | 1.16 g | 6 |
| 3-Methoxypropane-1-amine | 0.66 g | 7 |
| Cyclopentylamine | 0.63 g | 8 |
| 2-(morpholine-4-yl)ethanamine | 0.96 g | 9 |

The compounds listed in Table 1 are hydroxy amino polymers pursuant to the invention. They will be reacted with a trifunctional NCO-terminated prepolymer in the following. The production of the trifunctional NCO-terminated prepolymer is performed as follows:

Production of a Trifunctional NCO-Terminated Prepolymer 465 g of HDI and 2.35 g of benzoyl chloride were presented in a 1 l four-neck flask. 931.8 g of a trifunctional polyether of a molar mass of 4500, started on glycerin and an ethylene oxide content of 71% and a propylene oxide content of 29%, respectively related to the overall alkylene oxide content, were added within 2 hours at 80° C. and subsequently stirred for 1 hour. The surplus HDI was then distilled off through thin film distillation at 130° C. and 0.13 mbar. 980 g (71%) of the prepolymer is obtained with an NCO content of 2.37% and a viscosity of 4500 mPa/23° C. The residual monomer content was <0.03% HDI.

Tissue Adhesive 2.08 g (1 equivalent) of hydroxy amino polymer 2 were added to 2 g of the trifunctional NCO-terminated prepolymer and stirred well in a cup for 20 seconds. A thin layer of the polyurea/polyurethane system was then directly applied to the muscle tissue to be bonded. The time during which the adhesive system still had a low viscosity was determined as the processing time, such that it could be applied to the tissue without difficulty.

The time, after which the polyurea/polyurethane system was no longer tacky (tack free time) was measured through bonding tests with a glass rod. In doing so, the glass rod was touched to the layer from the polyurea/polyurethane system. If it no longer remained bonded, the system was considered to be tack free. In addition, the bonding strength was determined, in which the ends of two pieces of muscle tissue (1=4 cm, h=0.3 cm, b=1 cm) were coated with the polyurea/polyurethane system 1 cm apart and adhered in an overlapping manner. The bonding strength of the polyurea/polyurethane system was respectively tested through tension.

The reaction of the NCO-terminated prepolymer with hydroxy amino polymers from Table 1:

TABLE 2

| Hydroxy amino polymer | Hardening product number | Processing time | Tack free time | Adhesive strength |
|---|---|---|---|---|
| N-pentylamine/(2) | 2a | 1 min. 30 seconds | 3 min. | ++ |
| N-propylamine/(3) | 3a | 1 min. 20 seconds | 3 min. | + |
| N-butylamine/(4) | 4a | 1 min. 30 seconds | 3 min. | ++ |
| N-hexylamine/(5) | 5a | 1 min. 10 seconds | 3 min. 30 seconds | ++ |
| N-decylamine/(6) | 6a | 1 min. 20 seconds | 3 min. 30 seconds | ++ |
| 3-methoxypropane-1-amine/(7) | 7a | 1 min. 10 seconds | 4 min. | + |
| Cyclopentylamine/(8) | 8a | 1 min. 40 seconds | 6 min. | o |
| 2-(morpholine-4-yl)ethanamine/(9) | 9a | 1 min. | 7 min. | + |

The exothermic reaction of the hardening was between 23 and 25° C.

Determining the Biodegradability

The adhesive was applied to a tube (diameter: 0.5 cm, length: 2 cm) for hardening. The resulting 2.7 g heavy test sample was agitated in 10 ml of buffer solution (pH: 7.4, Aldrich: P-5368) at 60° C. or 37° C. in an agitation incubator with 150 RPM until the material was completely dissolved, i.e. without residuum.

All samples were fully degraded after 4 days at 60° C.

Measurement of Cytotoxicity of 2a

The hardened adhesive was tested for cytotoxicity according to ISO 10993-5:2009 with L 929 cells. The material proved to be non-cytotoxic.

The invention claimed is:

1. A polyurea/polyurethane system comprising
   an isocyanate functional prepolymer as a component A) obtained by reacting
      an aliphatic and/or aromatic polyisocyanate A1) with
      a polyol A2), which may have a number average molecular weight of ≥400 g/mol and an average OH functionality of 2 to 6,
   a hydroxy amino polymer as component B),
   wherein said hydroxy amino polymer comprises polyester polyol units, polyester-polyether polyol units, and/or polyether polyol units, having a share of oxyethylene units of 40 to 90% by weight, wherein said hydroxy amino polymer has a general formula (I)

$$\text{Starter}\left[\begin{array}{c}\text{O}\\\phantom{x}\\R6\end{array}\begin{array}{c}R5\\\phantom{x}\\R4\end{array}\right]_n\text{O}-A-\text{O}\left[\begin{array}{c}R6\\\phantom{x}\\R7\end{array}\begin{array}{c}R5\\\phantom{x}\\R4\end{array}\text{O}\right]_o\left[\phantom{x}\right]_m\text{H}, \quad (I)$$

wherein
   "starter" represents the radical of the H functional starter compound,
   A represents an aspartate group of the following structure of formulas (IIa) or (IIb)

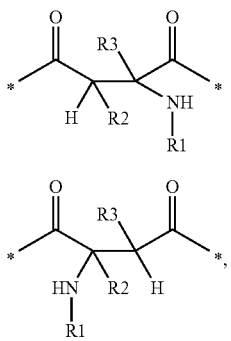

in which
R1 represent hydrogen or an aliphatic, cycloaliphatic or aromatic radical, which may also contain heteroatoms, nitrogen atoms or oxygen atoms as well as hydroxyl groups, R2 and R3 independently represent hydrogen or an aliphatic or aromatic radical and R2 and R3 may also be a component of a cycloaliphatic ring system, R4, R5, R6, and R7 independently represent hydrogen or an aliphatic or aromatic radical and R5 and R6 may also be a component of a cycloaliphatic ring system, l corresponds to the number of Zerewitinoff active hydrogen atoms of the H functional starter compound, m, n, and o are independently whole numbers, wherein n is 2 to 430, o=≥1 and m≥1, and wherein the equivalent molar mass of a structure shown in formula I does not exceed the value of 18900 g/mol, optionally organic fillers, which may have a viscosity measured according to DIN 53019 at 23° C. in the range of 10 to 6000 mPa, as a component C), a reaction product of the isocyanate functional prepolymer according to component A) with hydroxy amino functional compounds according to component B), and/or organic fullers according to component C) potentially as component D), and optionally water and/or a tertiary amine as a component E).

2. The polyurea/polyurethane system according to claim 1, wherein the hydroxy amino polymer is obtained by:
a) reacting an H functional starter compound bearing at least one Zerewitinoff active H atom with an unsaturated, cyclical carboxylic acid anhydride and at least one alkylene oxide compound for obtaining a prepolymer bearing hydroxyl groups,
b) adding a primary amine and/or an ammonia to the double bond(s) of the prepolymer bearing hydroxyl groups obtained according to step a) for obtaining the hydroxy amino polymer,
wherein the ratio of added amino groups to hydroxyl groups in a hydroxy amino polymer is at least 0.6.

3. The polyurea/polyurethane system according to claim 2, wherein the ratio of added amino groups to hydroxyl groups in said hydroxy amino polymer is 0.8 to 2.5, and/or wherein said hydroxy amino polymer has an OH functionality of 1.5 to 6.

4. The polyurea/polyurethane system according to claim 2, wherein said H functional starter compound has 1 to 35 Zerewitinoff active H atoms.

5. The polyurea/polyurethane system according to claim 2, wherein said unsaturated, cyclical carboxylic acid anhydride is selected from the group of unsaturated, cyclical dicarboxylic acid anhydrides, tetrahydrophthalic acid anhydride, and combinations thereof.

6. The polyurea/polyurethane system according to claim 2, wherein said alkylene oxide compound is selected from alkylene oxides with 2 to 24 carbon atoms.

7. The polyurea/polyurethane system according to claim 2, wherein a molar ratio between said alkylene oxide compound and carboxylic acid anhydride is at least 1:1.

8. The polyurea/polyurethane system according to claim 2, wherein said H functional starter compound is first reacted with an initial amount of alkylene oxide compound and then with the unsaturated, cyclical carboxylic acid anhydride and an additional amount of alkylene oxide compound.

9. The polyurea/polyurethane system according to claim 2, wherein the reaction of said H functional starter compound with said unsaturated, cyclical carboxylic acid anhydride and/or the addition of said alkylene oxide compound is performed using a double metal cyanide catalyst (DMC catalyst), wherein said DMC catalyst contains zinc hexacyanocobaltate (III), zinc hexacyanoiridate (III), zinc hexacyanoferrate (III), and/or cobalt (II) hexacyanocobaltate (III).

10. The polyurea/polyurethane system according to claim 2, wherein said H functional starter compound is first reacted with said unsaturated, cyclical carboxylic acid anhydride and subsequently with said alkylene oxide compound or wherein said H functional starter compound is simultaneously reacted with said unsaturated, cyclical carboxylic acid anhydride and said alkylene oxide compound, and/or wherein the process is conducted using an amine catalyst.

11. The polyurea/polyurethane system according to claim 1, wherein said polyol A2) contains polyester polyol and/or polyester-polyether polyol and/or polyether polyol.

12. The polyurea/polyurethane system according to claim 1, wherein said prepolymer A) has an average NCO functionality of 1.5 to 6.

13. The polyurea/polyurethane system according to claim 1, wherein a trifunctional polyol is used for producing component A.

14. The polyurea/polyurethane system according to claim 1, wherein said organic fillers of component C) are hydroxy functional compounds.

15. The polyurea/polyurethane system according to claim 1, wherein a component E) contains a tertiary amine of a general formula (IX),

in which $R_8$, $R_9$, and $R_{10}$ may independently be alkyl or heteroalkyl radicals having heteroatoms in an alkyl chain or at their ends, or $R_8$ and $R_9$ can form an aliphatic, unsaturated or aromatic heterocycle together with a nitrogen atom bearing them, which may potentially contain additional heteroatoms.

16. The polyurea/polyurethane system according to claim 1, wherein said tertiary amine is selected from the group consisting of triethanolamine, tetrakis (2-hydroxyethyl) ethylenediamine, N,N-dimethyl-2-(4-methylpiperazine-1-yl) ethanamine, and 2-{[2-(dimethylamino)ethyl](methyl)

amino}ethanol, 3,3',3''-(1,3,5-triazinane-1,3,5-triyl)tris(N,N-dimethyl-propane-1-amine).

17. The polyurea/polyurethane system according to claim 1, wherein said component E) contains 0.2 to 2.0% by weight of water and/or 0.1 to 1.0% by weight of said tertiary amine.

18. A dispensing system having two chambers for the polyurea/polyurethane system according to claim 1, wherein said component A) is contained in one chamber and said component B) and optionally components C), D), and E) of said polyurea/polyurethane system are contained in another chamber.

\* \* \* \* \*